United States Patent
Irisawa

(10) Patent No.: US 7,175,640 B2
(45) Date of Patent: Feb. 13, 2007

(54) VASCULAR INCISION APPARATUS

(75) Inventor: Yuichiro Irisawa, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 585 days.

(21) Appl. No.: 10/349,928

(22) Filed: Jan. 24, 2003

(65) Prior Publication Data
US 2003/0144679 A1   Jul. 31, 2003

(30) Foreign Application Priority Data
Jan. 25, 2002 (JP) ............. 2002-017153
Jul. 30, 2002 (JP) ............. 2002-222060

(51) Int. Cl.
*A61B 17/3209* (2006.01)
*A61B 17/3113* (2006.01)

(52) U.S. Cl. ................. 606/172; 606/170
(58) Field of Classification Search ............ 606/166, 606/167, 172
See application file for complete search history.

(56) References Cited

U.S. PATENT DOCUMENTS

| | | | | |
|---|---|---|---|---|
| 3,945,117 A * | 3/1976 | Beaver | ......... | 30/287 |
| 4,597,385 A | 7/1986 | Watson | | |
| 4,785,809 A | 11/1988 | Weinrib | | |
| 5,047,042 A * | 9/1991 | Jerath | ......... | 606/167 |
| 5,071,426 A * | 12/1991 | Dolgin et al. | ......... | 606/167 |
| 5,314,440 A * | 5/1994 | Shapiro | ......... | 359/676 |
| 5,545,172 A * | 8/1996 | Knepshield et al. | ......... | 606/166 |
| 5,776,154 A | 7/1998 | Taylor et al. | | |
| 5,893,861 A | 4/1999 | Yumoto | | |
| 6,048,354 A * | 4/2000 | Lawrence | ......... | 606/185 |
| 6,224,574 B1 * | 5/2001 | Al-Labban | ......... | 604/187 |
| 6,261,265 B1 * | 7/2001 | Mosseri | ......... | 604/198 |
| 6,908,476 B2 * | 6/2005 | Jud et al. | ......... | 606/205 |
| 2002/0177864 A1 * | 11/2002 | Camrud | ......... | 606/167 |

FOREIGN PATENT DOCUMENTS

FR   583 314   7/1928

* cited by examiner

*Primary Examiner*—Anhtuan T. Nguyen
*Assistant Examiner*—Elizabeth Houston
(74) *Attorney, Agent, or Firm*—Buchanan Ingersoll & Rooney PC

(57) ABSTRACT

A vascular incision apparatus is composed in part of a needle for puncturing a blood vessel and a cutter for making an incision in the blood vessel. The apparatus easily, rapidly and reliably creates a vascular incision of the desired length by employing an incision length controlling means to control the length of penetration by the needle into the blood vessel, or by controlling the distance between the respective needle points on first and second needles which face each other across a given distance, one of which needles is movable relative to the other.

31 Claims, 36 Drawing Sheets

VASCULAR INCISION APPARATUS

BACKGROUND OF THE INVENTION

1. Field of the Invention

The present invention relates to an apparatus for creating an incision in a patient's blood vessel.

2. Prior Art

Vascular incisions are typically made using an implement such as a scalpel or scissors.

For instance, in coronary artery bypass surgery and other vascular angiostomy techniques, when performing an end-to-side anastomosis between the internal thoracic artery and the left coronary artery, for example, first an incision is made in the left coronary artery, then the incision is anastomotized to the end of the internal thoracic artery. In such cases, the incision is formed with a scalpel or scissors, and the procedure is dependent on the skill of the surgeon. Moreover, the required incision length is typically arrived at by gradually enlarging a small initial incision through repeated use of the scalpel or scissors.

When creating an incision in a blood vessel with a scalpel or scissors, cutting must be carried out with utmost care to achieve an incision of the desired length. Such cutting is also time-consuming.

Even when an incision is made with great patience and care, the desired incision length is not always obtained. This approach thus lacks precision. Achieving the desired incision length in this way is especially difficult when the patient's heart is beating.

SUMMARY OF THE INVENTION

It is therefore an object of the present invention to provide an apparatus which enables an incision of the target, or desired, length to be easily, rapidly and reliably created in a blood vessel.

This and related objects are attained by the present invention, which provides an apparatus for creating an incision in a patient's blood vessel.

In a first aspect, the invention provides a vascular incision apparatus which includes a body; a puncturing and cutting member having a needle with a sharp point for penetrating a blood vessel and a cutter for making an incision in the blood vessel, which cutter is disposed proximal to the needle; and incision length controlling means for controlling the length of the incision made by the puncturing and cutting member.

In one embodiment of the apparatus according to this first aspect of the invention, the incision length controlling means has a stopper arm with a stop thereon that comes into resting contact with the puncturing and cutting member at a boundary between the needle and the cutter or at the needle. The contact by the stop with the puncturing and cutting member controls the length of penetration by the needle into the blood vessel. The stopper arm is provided such as to enable repositioning thereof relative to the puncturing and cutting member between a first position which prevents the cutter from cutting the blood vessel and a second position which allows the cutter to cut the blood vessel. The stop typically separates away from the puncturing and cutting member when the stopper arm assumes the second position. It is preferable for the apparatus to additionally have restoring means for returning the stopper arm to the first position. The puncturing and cutting member may be disposed at one end of the body and the stopper arm may be linearly movable or rotatable with respect to the body.

It is advantageous for the puncturing and cutting member to be movable with respect to the body, and for the apparatus to have a control member for effecting movement by the puncturing and cutting member. Repositioning of the stopper arm may be coupled to movement by the puncturing and cutting member.

In this and other embodiments of the first aspect of the invention, the apparatus may have an incision length adjusting mechanism for adjusting the incision length controlled by the incision length controlling means. It is advantageous for the incision length adjusting mechanism to adjust the length of the incision made in the blood vessel by changing the place on the puncturing and cutting member at which the stop comes into contact therewith when the stopper arm is in the first position. The incision length adjusting mechanism may have a holder for holding the stopper arm such as to allow movement thereof in the lengthwise direction of the needle, and a control member for effecting movement by the stopper arm in the lengthwise direction of the needle.

In the apparatus according to this first aspect of the invention, the needle may curved on at least a distal end thereof. Moreover, the puncturing and cutting member may be freely detachable from the body.

In a second aspect, the invention provides a vascular incision apparatus which includes puncturing and cutting means having a first needle with a sharp point for penetrating a blood vessel, a second needle with a sharp point for penetrating the blood vessel, which point on the second needle lies opposite the point on the first needle and is initially separated therefrom by a predetermined distance, and at least one cutter for making an incision in the blood vessel, which cutter is provided on a proximal end side of the first needle, on a proximal end side of the second needle or on the proximal end sides of both needles, wherein one of the needles is movable relative to the other needle. The apparatus also has control means for effecting movement by at least one of the two needles in a direction that brings the point of the first needle and the point of the second needle into close mutual proximity. The distance initially separating the point of the first needle from the point of the second needle is substantially equal to the length of the incision to be made in the blood vessel by the cutter.

The apparatus according to the second aspect of the invention may have means for urging a given portion of the puncturing and cutting means in a direction which separates the point on the first needle and the point on the second needle, means for controlling a closest approach state in which the first and second needles are in closest mutual proximity, and/or means for controlling a maximum separation state in which the first and second needles are furthest apart from each other. In an apparatus having such a maximum separation state controlling means, this means may include an incision length adjusting mechanism for modifying the maximum separation state to adjust the maximum distance between the point on the first needle and the point on the second needle.

The apparatus according to this aspect of the invention may have an incision length adjusting mechanism for adjusting the distance of maximum separation between the point on the first needle and the point on the second needle. In one configuration, one of the needles has on at least a distal end thereof a groove which engages a distal end of the other needle. In another configuration, one of the needles has on at least a distal end thereof an aperture which receives a distal end of the other needle. The aperture-bearing distal end of the needle may have a face which is beveled toward the distal end of the needle. At least one of the needles in this aspect of the invention may have a distal end which is beveled downward.

The apparatus according to the second aspect of the invention typically has a body with a distal end and a proximal end, the body having a puncturing and cutting means provided at the distal end thereof. The control means in the apparatus typically includes an actuating element which is provided on the body at the proximal end thereof. In one configuration, the apparatus according to this aspect of the invention may additionally have a pair of supports, at least one of which is rotatable about a pivot, wherein the first needle is provided on one of the pair of supports and the second needle is provided on the other support. In this configuration, one of the pair of supports may be fixed with respect to the body and the other may be rotatable about a pivot, and the control means may have an actuating element provided movably on the body at the proximal end thereof and a coupling member for coupling the actuating element with the rotatable support.

In another configuration, the apparatus may additionally have a pair of supports, at least one of which is movable with respect to the body, wherein the first needle is provided on one of the supports and the second needle is provided on the other support. In this configuration, one of the pair of supports may be fixed with respect to the body and the other may be movable with respect to the body, and the control means may have an actuating element provided movably on the body at the proximal end thereof and a coupling member for coupling the actuating element with the movable support.

In the apparatus according to this second aspect of the invention, at least a portion of the body may be deformable and the apparatus may be so constructed as to be capable of retaining the deformed shape.

In the apparatus according to the above-described first or second aspect of the invention, the needle and cutter may be integrally formed. Moreover, it is preferable for the needle and the blade on the cutter to form an angle therebetween of at most 180°.

In the apparatus according to the second aspect of the invention, the needles are typically freely detachable from the puncturing and cutting means at specific places thereon.

BRIEF DESCRIPTION OF THE DRAWINGS

The objects, features and advantages of the invention will become more apparent from the following detailed description taken in conjunction with the accompanying drawings, in which.

DESCRIPTION OF THE PREFERRED EMBODIMENTS

Reference will now be made in detail to the preferred embodiments of the invention shown in the accompanying drawings.

As noted above, FIG. 1 is a side view of a first embodiment of the vascular incision apparatus of the invention; FIG. 2 is a front view of the apparatus of FIG. 1; FIG. 3 is a front view of the stopper arm in the apparatus of FIG. 1; FIG. 4 is a side view of the apparatus of FIG. 1, showing the stopper arm separated from the puncturing and cutting member; and FIG. 5 is a side view, in cross section, of the vicinity of the bottom end of the apparatus of FIG. 4.

Figure 1:
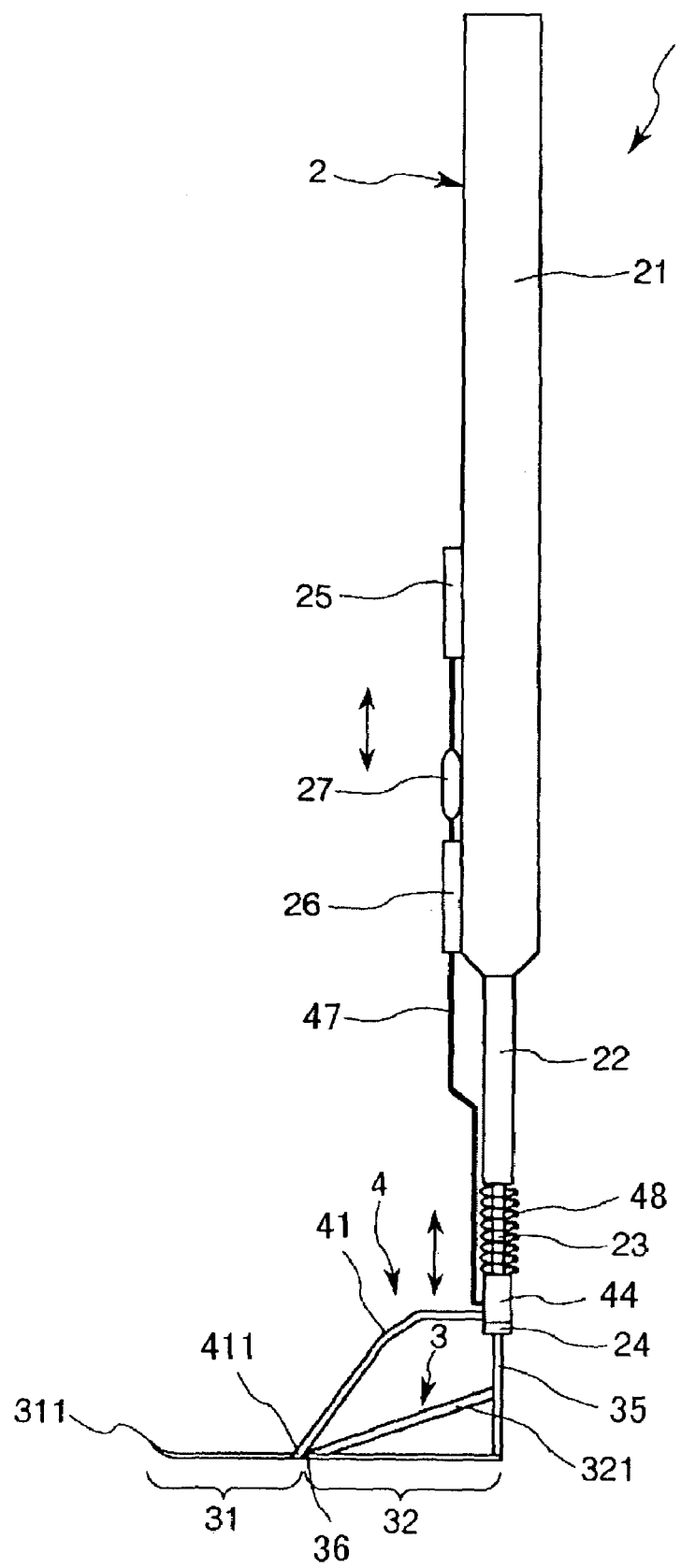
FIG. 1 is a side view of a first embodiment of the vascular incision apparatus of the present invention.
Figure 2:
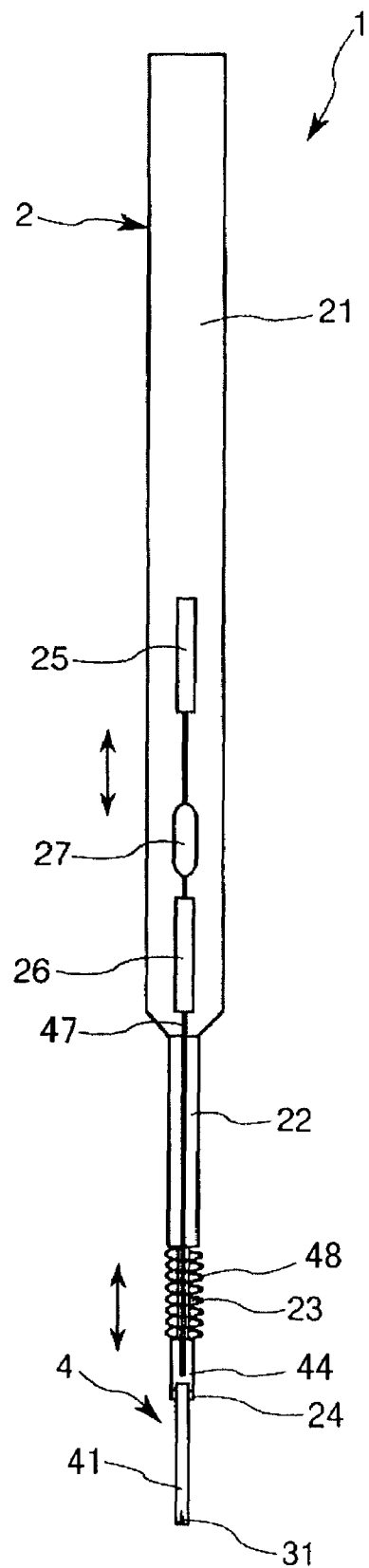
FIG. 2 is a front view of the apparatus of FIG. 1.
Figure 3:
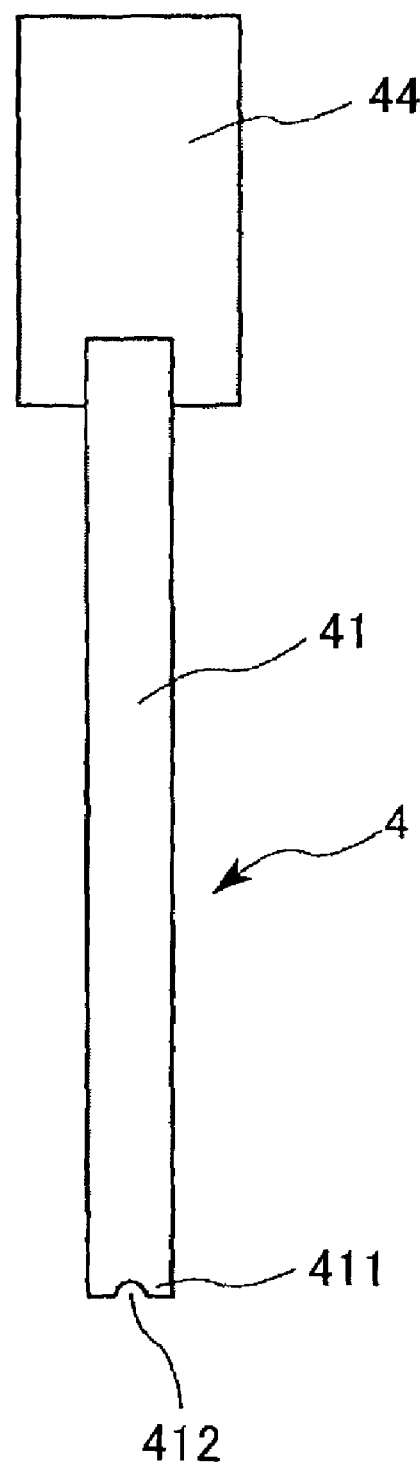
FIG. 3 is a front view of the stopper arm in the apparatus of FIG. 1.
Figure 4:
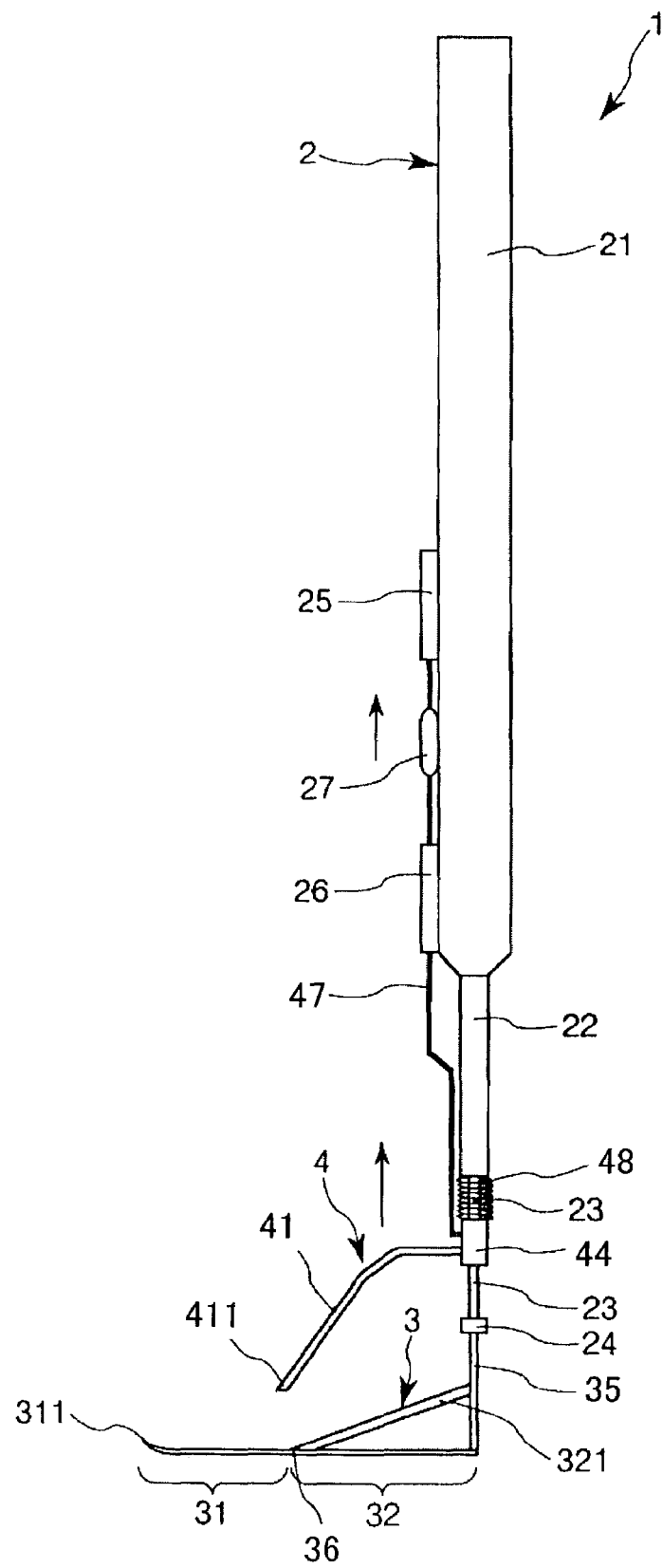
FIG. 4 is a side view of the apparatus of FIG. 1, showing the stopper arm separated from the puncturing and cutting member.
Figure 5:
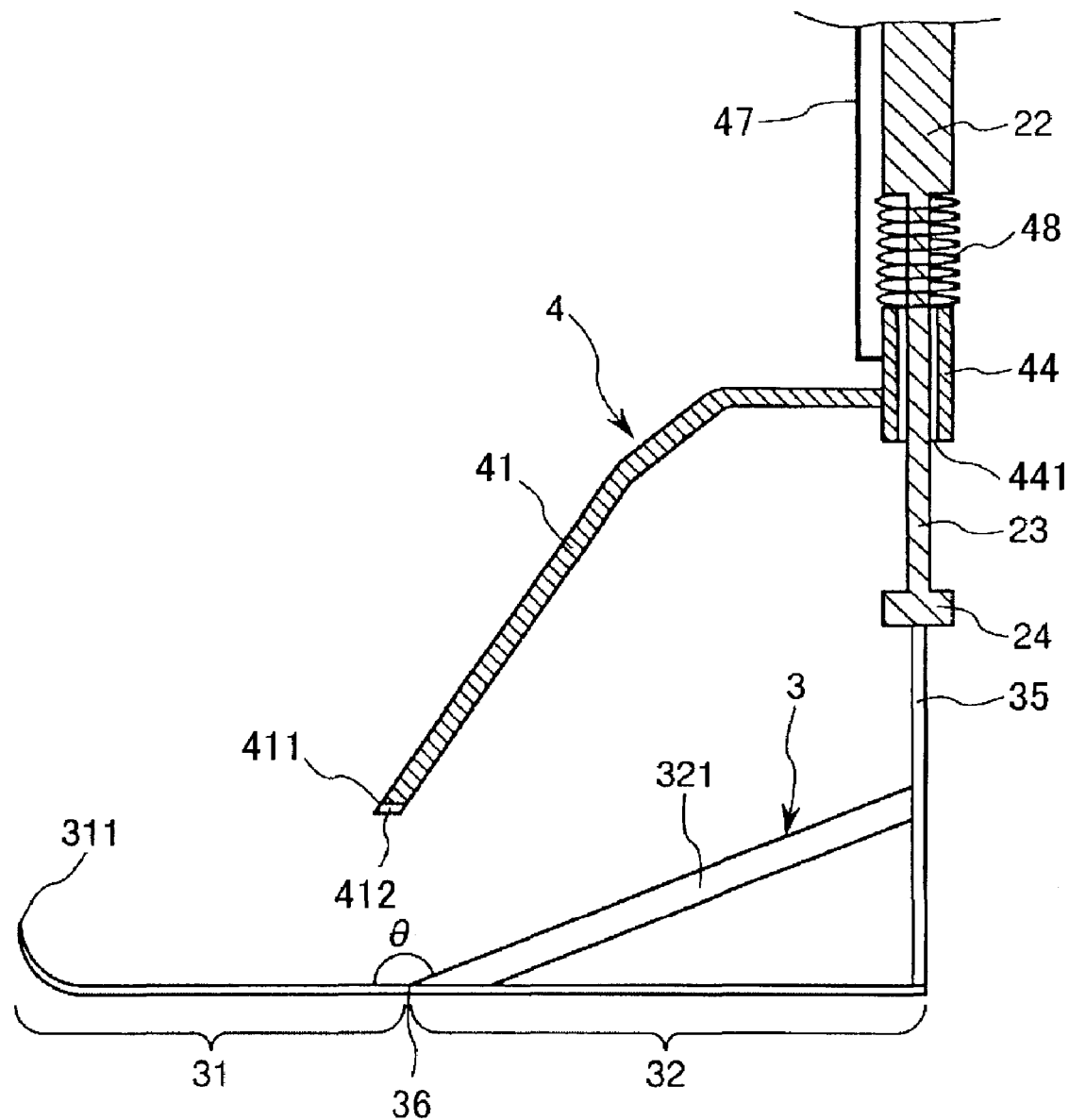
FIG. 5 is a side view, in cross section, of the vicinity of the bottom end of the apparatus of FIG. 4.

In FIGS. 1, 4 and 5, the puncturing and cutting member side of the vascular incision apparatus is referred to as the "bottom end" or "bottom," and the body side of the apparatus is referred to as the top end" or "top." The left side with respect to the thus-defined "bottom" and "top" of the apparatus is referred to herein as the "distal end," and the right side as the "proximal end." Similarly, in FIGS. 2 and 3, the puncturing and cutting member side of the vascular incision apparatus is referred to as the "bottom end" or "bottom," and the body side is referred to as the "top end" or "top."

The apparatus 1 shown in these diagrams is an instrument for creating an incision in a blood vessel. The apparatus 1 has a body 2, a puncturing and cutting member 3 for making a vascular incision, and an incision length controlling means 4 for controlling the length of the incision made by the puncturing and cutting member 3. These constituent elements are each in turn described below.

Referring to FIGS. 1 and 2, the body 2 has an elongated handle 21. The user grasps this handle 21 with the hand and fingers when using the apparatus 1.

The handle 21 has at a bottom end thereof an attachment section 22 for attaching thereto the puncturing and cutting member 3 and a stopper arm 41, both of which are subsequently described.

The attachment section 22 is substantially cylindrical and has formed near a bottom end thereof a reduced diameter portion 23 of smaller diameter than the attachment section 22. In addition, the attachment section 22 has formed at the bottom end thereof a flange 24 of larger diameter than the reduced diameter portion 23. Hence, the attachment section portions 22 and 24 situated above and below the reduced diameter portion 23 both have larger diameters than the reduced diameter portion 23.

The handle 21 has formed thereon, at positions above the attachment section 22, a pair of holders 25 and 26 for movably holding a rod-like element 47, which is described subsequently.

The holders 25 and 26 are arranged on the handle 21 such that one of the holders 25 is located on an upper side thereof and the other holder 26 is located on a lower side, with the two holders 25 and 26 being separated in the vertical direction by a given distance therebetween.

These holders 25 and 26 each have formed therein a bore sized to receive the rod-like element 47 for insertion therein or passage therethrough.

As shown in FIG. 5, the puncturing and cutting member 3 has a needle 31 with a sharp point 311 for penetrating the blood vessel, a cutter 32, situated proximal to the needle 31, for making an incision in the blood vessel, and a support 35 situated proximal to the cutter 32.

The puncturing and cutting member 3 is fixedly attached to the bottom end of the body 2. In FIG. 5, a top end of the support 35 on the puncturing and cutting member 3 is joined to a bottom end of the flange 24 on the attachment section 22 of the handle 21.

In the first embodiment of the vascular incision apparatus of the invention, the puncturing and cutting member 3 may be provided so as to be freely detachable from the body 2. That is, the puncturing and cutting member 3 may be replaceable.

The distal end portion of the needle 31, which is the side having a sharp point 311, is upwardly curved, and the portion of the needle 31 proximal thereto is substantially linear. Curving the needle 31 over at least, and preferably only, the distal end portion thereof enables the needle 31 to more easily penetrate the blood vessel.

The cutter 32 is substantially triangular in side shape. The blade 321 is formed on the top of the cutter 32. In another arrangement, the cutter 32 may be composed of a section which is an extension of the needle 31 and a blade 321 formed on the top side of the extension. In this arrangement, the extension and the blade 321 are joined together at the distal ends thereof, and the extension and the blade 321 are separately joined at their respective proximal ends to the support 35, giving the cutter 32 a substantially triangular shape.

The angle θ (in degrees) formed by the needle 31 and the blade 321 on the cutter 32 in the vicinity of a boundary 36 between the needle 31 and the cutter 32, while not subject to any particular limitation, is preferably not more than 180°, and more preferably about 120 to 180°. A vascular incision can be more easily created at an angle θ of not more than 180°.

The needle 31 and the cutter 32 have respective lengths which are not subject to any particular limitation and may be suitably set according to various conditions, such as the length of the vascular incision to be made.

In this arrangement, when the subsequently described stopper arm 41 is in a "first position," the distance from the place where a stop 411 on the stopper arm 41 comes to rest against the puncturing and cutting member 3 (in the present embodiment, such contact occurs at the boundary 36 between the needle 31 and cutter 32; in other embodiments, it may occur at either the needle 31 or the boundary 36) to the needle point 311 will become substantially the length of the incision made by the apparatus 1.

The needle 31 may be made of any suitable material, examples of which include various metals (e.g., stainless steel, titanium, steel, iron, and alloys thereof) and ceramics.

The cutter 32 may likewise be made of any suitable material, examples of which include various metals (e.g., stainless steel, titanium, steel, iron, and alloys thereof) and ceramics.

In the present embodiment, the needle 31 and the cutter 32 have an integral construction which may be arrived at either by integrally forming the needle 31 with the cutter 32, or by separately forming the needle 31 and the cutter 32, then uniting the two.

Figure 10:
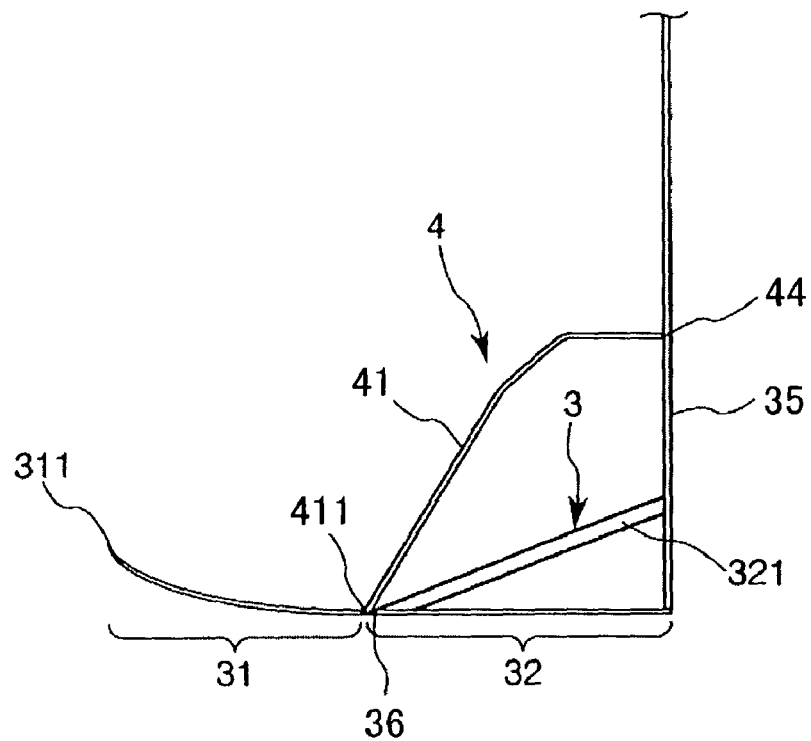
FIG. 10 is a side view showing another configuration of the puncturing and cutting member in the apparatus of the present invention.
Figure 11:
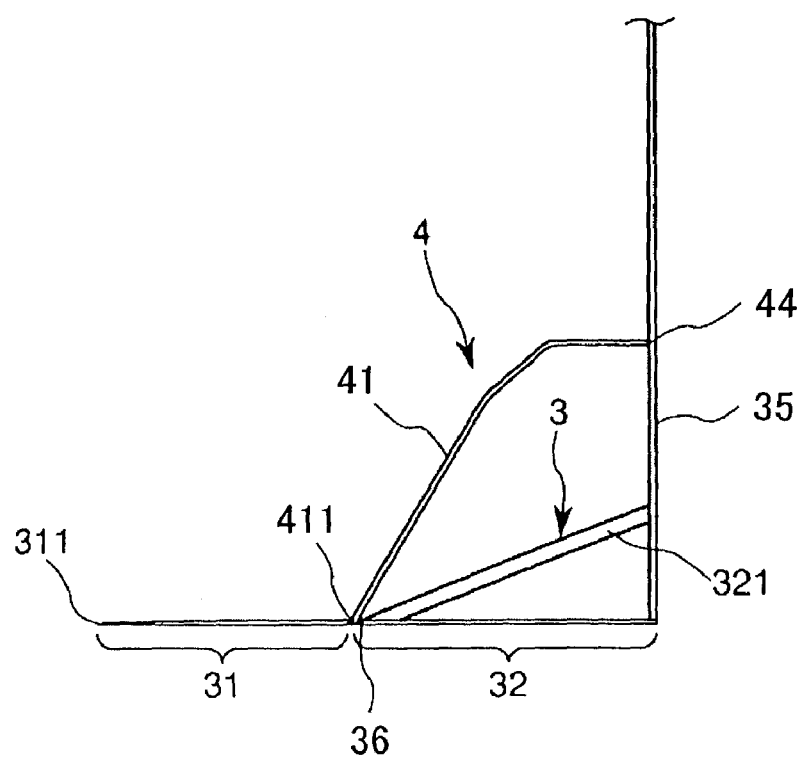
FIG. 11 is a side view showing yet another configuration of the puncturing and cutting member in the apparatus of the present invention.

The needle 31 and cutter 32 of the puncturing and cutting member 3 each have shapes which are not limited to those shown in the foregoing diagrams. For example, the needle 31 may be curved upward over its entire length in the manner shown in FIG. 10, or may be substantially straight over its entire length in the manner shown in FIG. 11. Moreover, the blade 321 on the cutter 32 may be curved or bent at its top end.

Referring to FIG. 5, the incision length controlling means 4 has a stopper arm 41 which is provided so as to be repositionable (in the present embodiment, linearly movable) with respect to the puncturing and cutting member 3 and the body 2.

The stopper arm 41 is shaped substantially as a somewhat curved or bent rod and has at a distal end (bottom end) thereof a stop 411 which comes to rest against the boundary 36 between the needle 31 and the cutter 32.

Referring to FIG. 3, the stop 411 has formed therein a groove 412 which engages the puncturing and cutting member 3 (at the boundary 36 in the present embodiment).

As shown in FIG. 5, the groove 412 extends in the direction of the needle 31.

Referring still to FIG. 5, the stopper arm 41 has a substantially cylindrical slider 44 provided at a proximal end (top end) thereof.

The slider 44 has a through-hole 441 through which the reduced diameter portion 23 of the attachment section 22 passes in an arrangement that enables the slider 44 to move vertically along the reduced diameter portion 23.

The stopper 41 may be made of any suitable material, examples of which include various metals (e.g., stainless steel, titanium, steel, iron, and alloys thereof) and plastics.

As shown in FIG. 1, at a part of the reduced diameter portion 23 located above the slider 44, a coil spring (urging member) 48 is held in a contracted state between a top end of the slider 44 and a bottom end of the non-reduced diameter portion of the attachment section 22. The restoring force (elastic force) of the coil spring 48 urges the slider 44 downward toward the puncturing and cutting member 3 and against the flange 24.

At the same time, the stop 411 on the stopper arm 41 comes to rest against the boundary 36, and the groove 412 on the stop 411 engages the boundary 36. The condition in which, as shown in FIG. 1, the stop 411 on the stopper arm 41 comes to rest against the puncturing and cutting member 3, and more specifically the boundary 36 of the puncturing and cutting member 3, is referred to herein as the "first position" of the stopper arm 41.

When the stopper arm 41 is in this first position, the stop 411 rests against the boundary 36, thereby restricting the length of vascular penetration by the needle 31 to the distance from the needle point 311 to the boundary 36 and preventing the cutter 32 from cutting the blood vessel.

In this condition, the slider 44 is urged downward by the coil spring 48 and the stop 411 engages the boundary 36, enabling the stopper arm 41 to be reliably held in the first position.

Moreover, referring again to FIG. 1, one end, and specifically the bottom end, of the relatively slender rod-like, or wire-like, element 47 is joined to the slider 44. The other end, and specifically the top end, of the rod-like element 47 passes through the bore in the lower holder 26 and is inserted within the bore in the upper holder 25 so as to make the rod-like element 47 vertically movable.

A control member 27 is joined to the rod-like element 47 between the upper and lower holders 25 and 26. In the normal state, i.e., when the movement operation subsequently described is not carried but, this control member 27 is situated near the lower holder 26.

As shown in FIG. 4, moving the control member 27 upward (movement operation) against the restoring force of the coil spring 48 causes the slider 44, via the rod-like element 47, to travel upward along the reduced diameter portion 23. The stopper arm 41 thus moves upward and away from the puncturing and cutting member 3, causing the stop 411 and the groove 412 thereon to separate from the boundary 36. The condition in which, as shown in FIG. 4, the stop 411 on the stopper arm 41 separates away from the puncturing and cutting member 3, and more specifically the boundary 36 of the puncturing and cutting member 3, so as to make it possible for the cutter 32 to cut the blood vessel is referred to herein as the "second position" of the stopper arm 41.

Next, when the control member 27 is released, as shown in FIG. 1, the slider 44 moves downward along the reduced diameter portion 23 under the restoring force of the coil spring 48. This causes the stopper arm 41 to move downward, bringing the stop 411 to rest against the boundary 36 so that the groove 412 on the stop 411 engages the boundary 36, returning the stopper arm 41 to the first position.

Therefore, the first embodiment of the vascular incision apparatus 1 of the invention has a restoring means which returns the stopper arm 41 to the first position under urging by the coil spring 48.

In the apparatus 1 according to this first embodiment, the stopper arm 41 may be alternatively configured such that, when it is in the first position, the stop 411 thereon rests against the needle 31.

In the apparatus 1 according to the first embodiment of the invention, the puncturing and cutting member 3 is described as being fixedly attached to the body 2. However, in a preferred variation of the same embodiment, it is advantageous for the puncturing and cutting member 3 to be configured so as to be freely detachable from the body 2, and thus replaceable. Should the puncturing and cutting member 3 undergo breakage, damage or deterioration, such an arrangement would allow replacement of the puncturing and cutting member 3 alone, resulting in lower user costs than if the entire apparatus 1 had to be replaced. Moreover, the vascular incision may be set to the desired length by having on hand at the point of use a plurality of such puncturing and cutting members 3 with needles 31 of varying length, and selecting and mounting the most appropriate puncturing and cutting member 3 from among these.

The method of use, or operation, of the vascular incision apparatus 1 according to this embodiment is now described.

FIGS. 6 to 9 is a sequence of schematic views illustrating how the vascular incision apparatus 1 shown in FIG. 1 works. In FIGS. 6 to 9, the blood vessel 100 side is referred to as the "bottom end" or "bottom," and the apparatus 1 side is referred to as the "top end" or "top." The left side with respect to the thus-defined "bottom" and "top" is referred to as the "distal end," and the right side as the "proximal end."

When an incision is to be created in a blood vessel 100 using the vascular incision apparatus 1 of the invention, a specific apparatus 1 appropriate for the desired length of the incision in the blood vessel 100 is prepared ahead of time for use.

Figure 6:
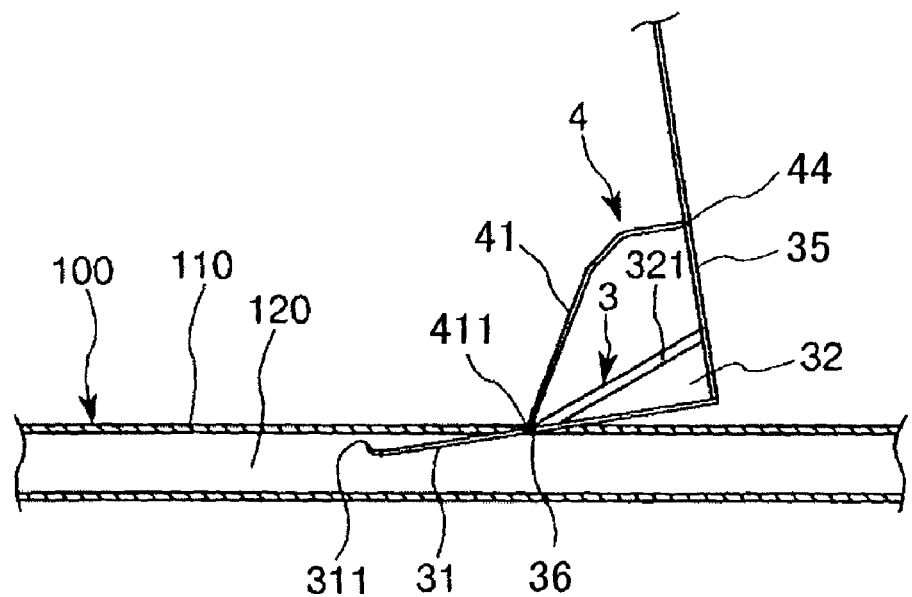
FIGS. 6 to 9 is a sequence of schematic views illustrating how the apparatus of FIG. 1 works.

To create the incision, first the user grasps the handle 21 of the apparatus 1 with the hand and fingers. Then, as shown in FIG. 6, the user penetrates the wall 110 of the vessel 100 at an initial cutting position with the sharp point 311 of the needle 31 on the puncturing and cutting member 3, and inserts the needle 31 into the lumen 120 of the vessel 100 until further insertion is stopped by the stopper arm 41.

Figure 7:
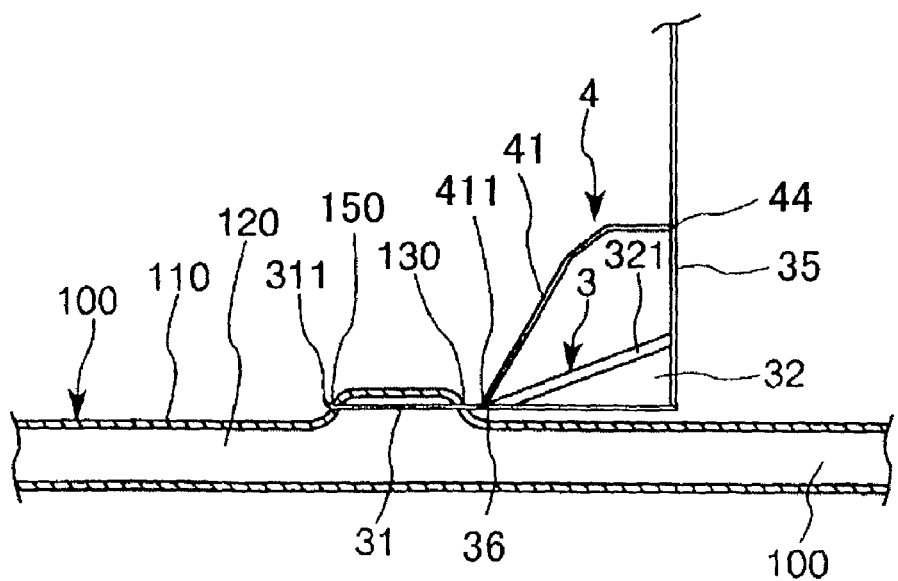

Next, as shown in FIG. 7, the point 311 of the needle 31 is thrust back out through the wall 110 of the vessel 100 from the lumen 120 thereof.

Because the length of the incision in the blood vessel 100 is restricted by the stopper arm 41 to the distance from the point 311 of the needle 31 to the boundary 36, during this step, the user has merely to push the point 311 of the needle 31 out through the wall 110 of the vessel 100 at a final cutting position thereon.

The foregoing procedure establishes the site and length of the incision in the blood vessel 100. That is, the incision site extends from the entry opening 130 where the needle point 311 enters the blood vessel 100 to the exit opening 150 where the point 311 is thrust back out of the vessel 100. The incision length is the length between the two openings.

Figure 8:
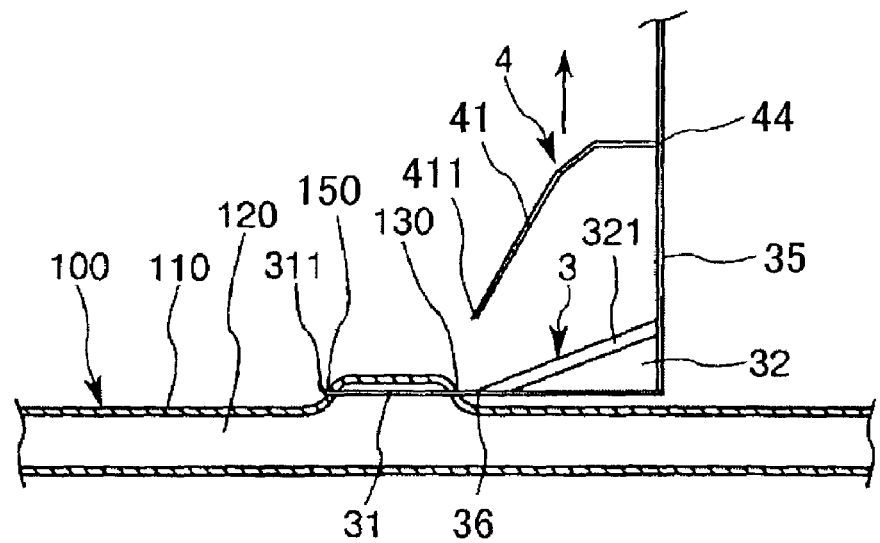

Next, the control member 27 is moved upward as mentioned above. This causes the stopper arm 41 to move linearly upward as shown in FIG. 8, separating away the stop 411 from the boundary 36.

Figure 9:
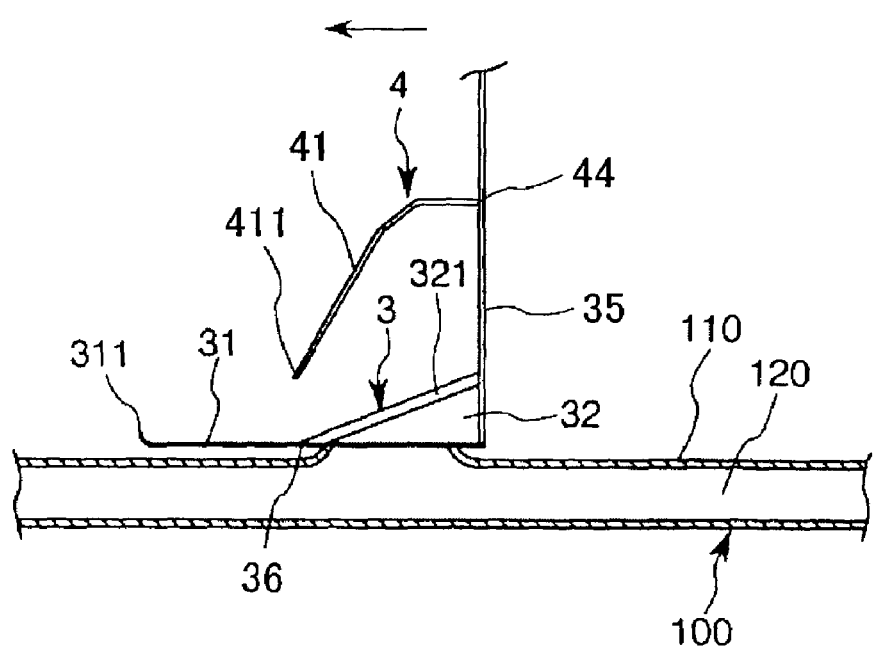

Next, as shown in FIG. 9, the user advances the apparatus 1 distally in the direction of the arrow. As the cutter 32 travels from entry opening 130 to exit opening 150 in the blood vessel 100, the blade 321 on the cutter 32 cuts open the wall 110 of the vessel 100 between entry opening 130 and exit opening 150.

When incision of the vessel 100 is complete, the control member 27 is released as noted above, allowing the stopper arm 41 to move downward so that the stop 411 once again comes to rest against the boundary 36.

The vascular incision apparatus 1 thus controls, by means of the stopper arm 41, the length of the incision created in the blood vessel 100, resulting in an incision which extends between the entry opening 130 and the exit opening 150 in the vessel 100 shown in FIG. 7. This enables the blood vessel 100 to be easily and reliably incised to the desired length.

Also, because the area to be incised is the interval between the entry opening 130 and the exit opening 150 in the blood vessel 100 shown in FIG. 7, the incision can be completed in a single action. This enables a blood vessel to be rapidly incised to the desired length.

Figure 12:
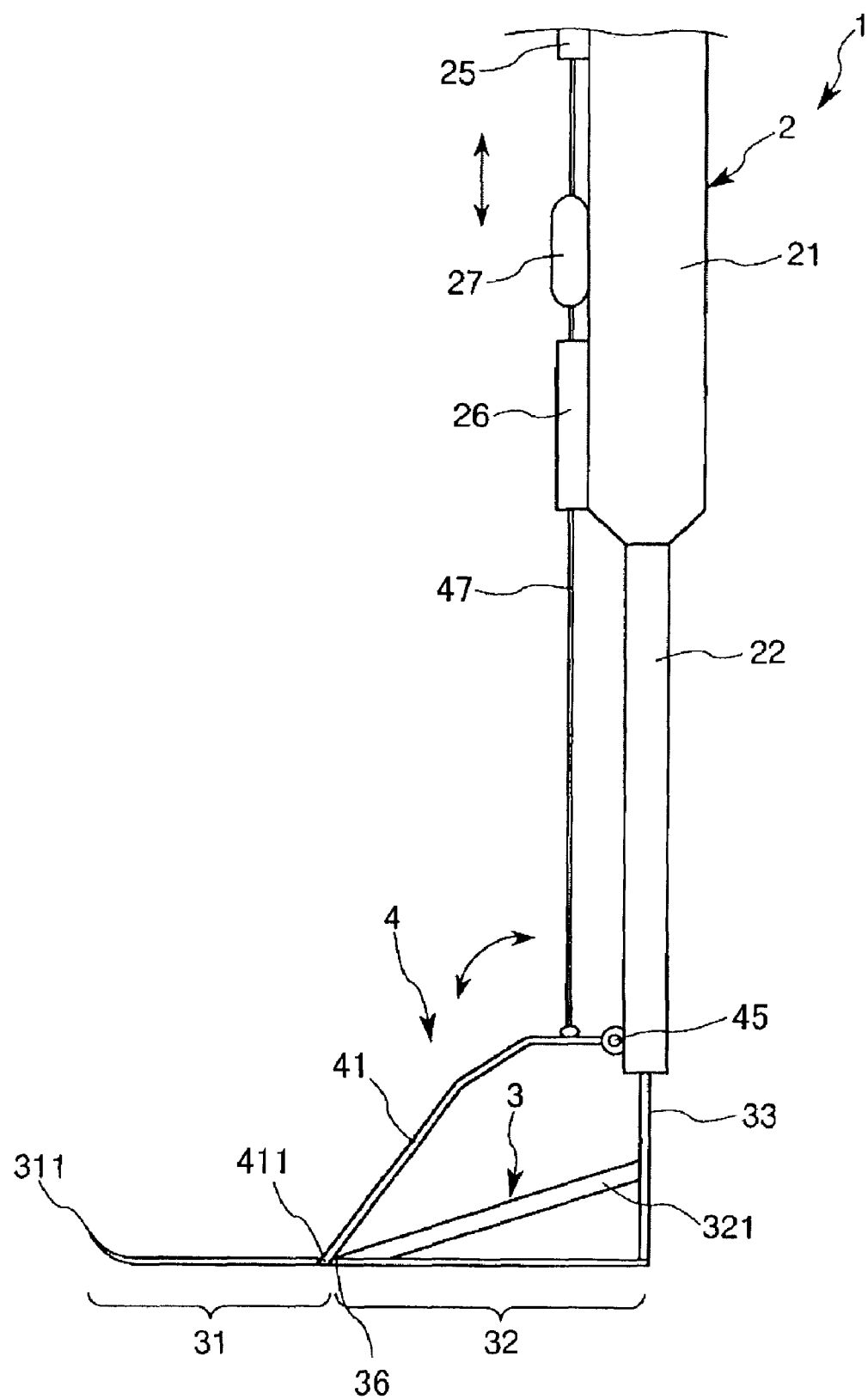
FIG. 12 is a side view of a second embodiment of the vascular incision apparatus of the invention.
Figure 13:
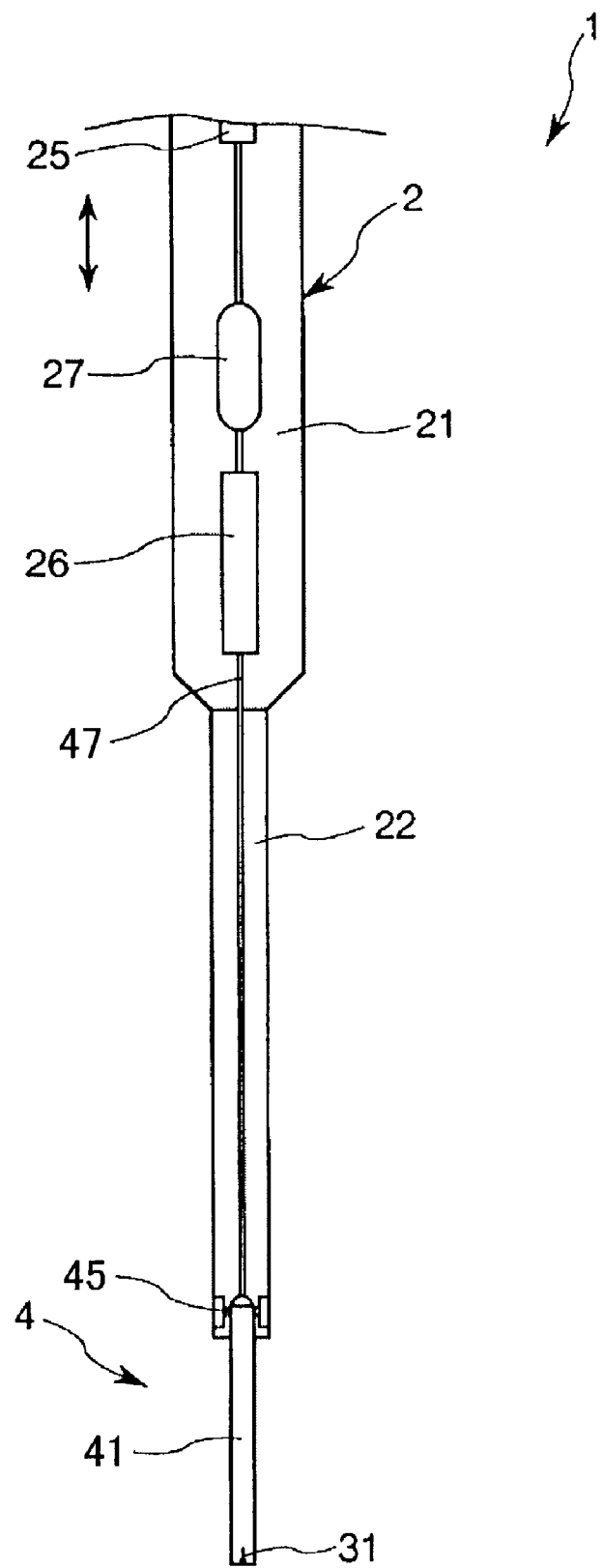
FIG. 13 is a front view of the apparatus of FIG. 12.
Figure 14:
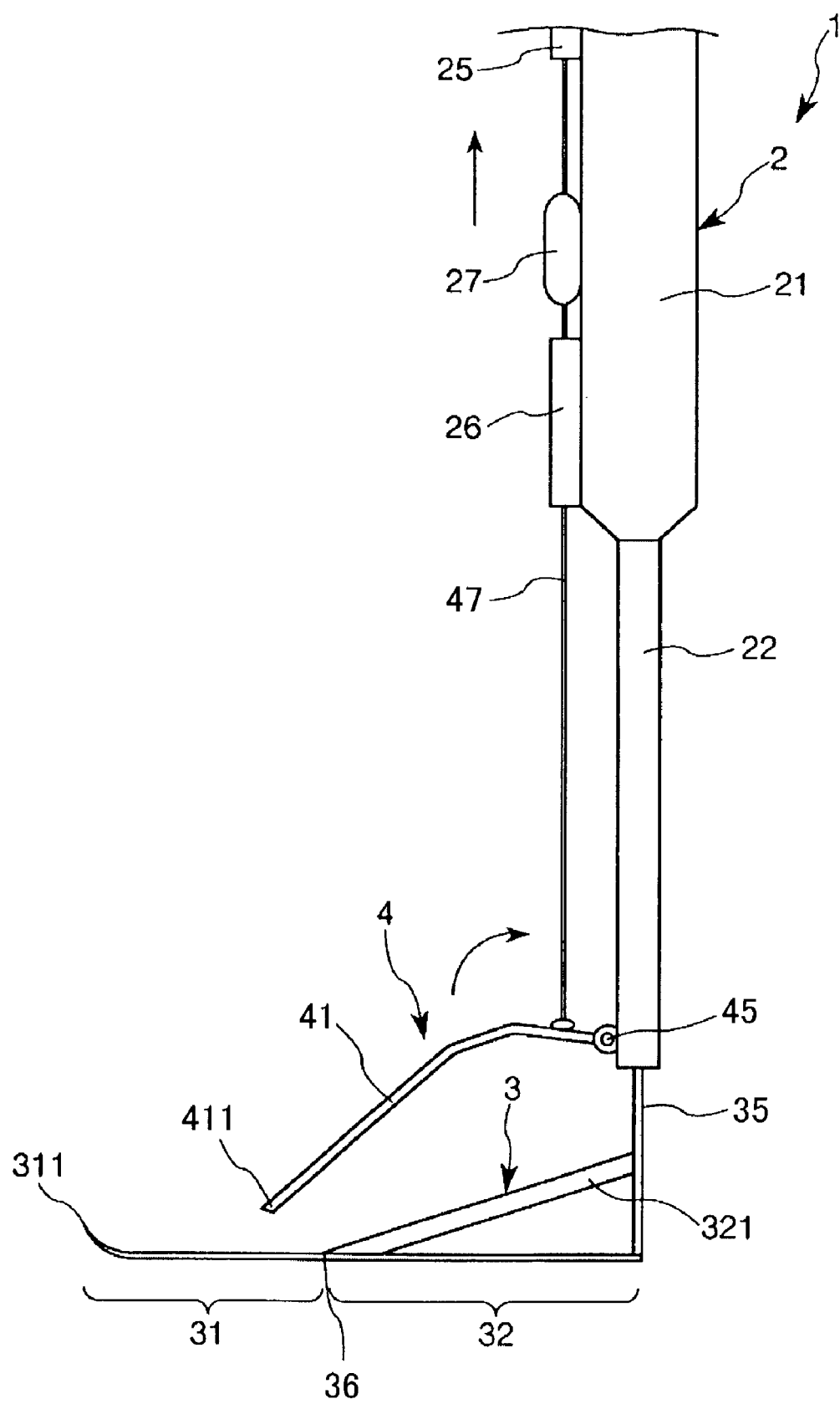
FIG. 14 is a side view of the apparatus of FIG. 12, showing the stopper arm separated from the puncturing and cutting member.

A second embodiment of the vascular incision apparatus according to the present invention is now described. FIG. 12 is a side view of a second embodiment of the vascular incision apparatus of the invention; FIG. 13 is a front view of the apparatus of FIG. 12; and FIG. 14 is a side view of the apparatus of FIG. 12, showing the stopper arm separated from the puncturing and cutting member.

The second embodiment of the inventive vascular incision apparatus is described below with particular reference to those features which differ from the foregoing first embodiment of the invention. Descriptions of like features are omitted. In FIGS. 12 and 14, the puncturing and cutting member side of the vascular incision apparatus is referred to as the "bottom end" or "bottom," and the body side of the apparatus is referred to as the top end" or "top." The left side with respect to the thus-defined "bottom" and "top" of the apparatus is referred to herein as the "distal end," and the right side as the "proximal end." Similarly, in FIG. 13, the puncturing and cutting member side of the vascular incision apparatus is referred to as the "bottom end" or "bottom," and the body side is referred to as the "top end" or "top."

As illustrated in these diagrams, in the second embodiment of the inventive vascular incision apparatus 1, the stopper arm 41 is provided so as to be rotatable with respect to the body 2. That is, the stopper arm 41 has formed at the proximal end thereof a pivot 45, and is disposed at the bottom end of the attachment section 22 on the handle 21 so as to be rotatable about the pivot 45.

The bottom end of the rod-like element 47 is joined, near the pivot 45, to the proximal end side of the stopper arm 41.

Operation of this vascular incision apparatus 1 is now described.

Referring to FIG. 14, when the user moves the control member 27 upward (direction of arrow), the stopper arm 41 rotates a predetermined amount in the clockwise direction (direction of arrow) about the pivot 45. This causes the stop 411 on the stopper arm 41, and thus the groove 412 on the stop 411, to separate away from the boundary 36.

In the state shown in FIG. 14 (with stopper arm 41 in second position), the stop 411 separates away from the boundary 36, making it possible for the cutter 32 to make an incision in the blood vessel.

Next, referring to FIG. 12, moving the control member 27 downward causes the stopper 41 to rotate a predetermined amount in the counterclockwise direction about the pivot 45. The stop 411 on the stopper arm 41 thus comes to rest against the boundary 36 and the groove 412 on the stop 411 engages with the boundary 36, returning the stopper arm 41 to the first position.

In the state illustrated in FIG. 12 (stopper arm 41 in first position), the stop 411 rests against the boundary 36, thereby restricting the length of penetration by the needle 31 into the blood vessel to the distance from the point 311 on the needle 31 to the boundary 36, and preventing the blood vessel from being cut by the cutter 32.

The advantageous effects provided by this vascular incision apparatus 1 are similar to the effects achievable with the first embodiment of the inventive apparatus described above.

In this second embodiment, as in the first embodiment described above, a restoring means (e.g., a spring or other urging member) may be provided which returns the stopper arm 41 to the first position. Other variations and modifications of the type discussed above in connection with the first embodiment may similarly be applied here.

Figure 15:
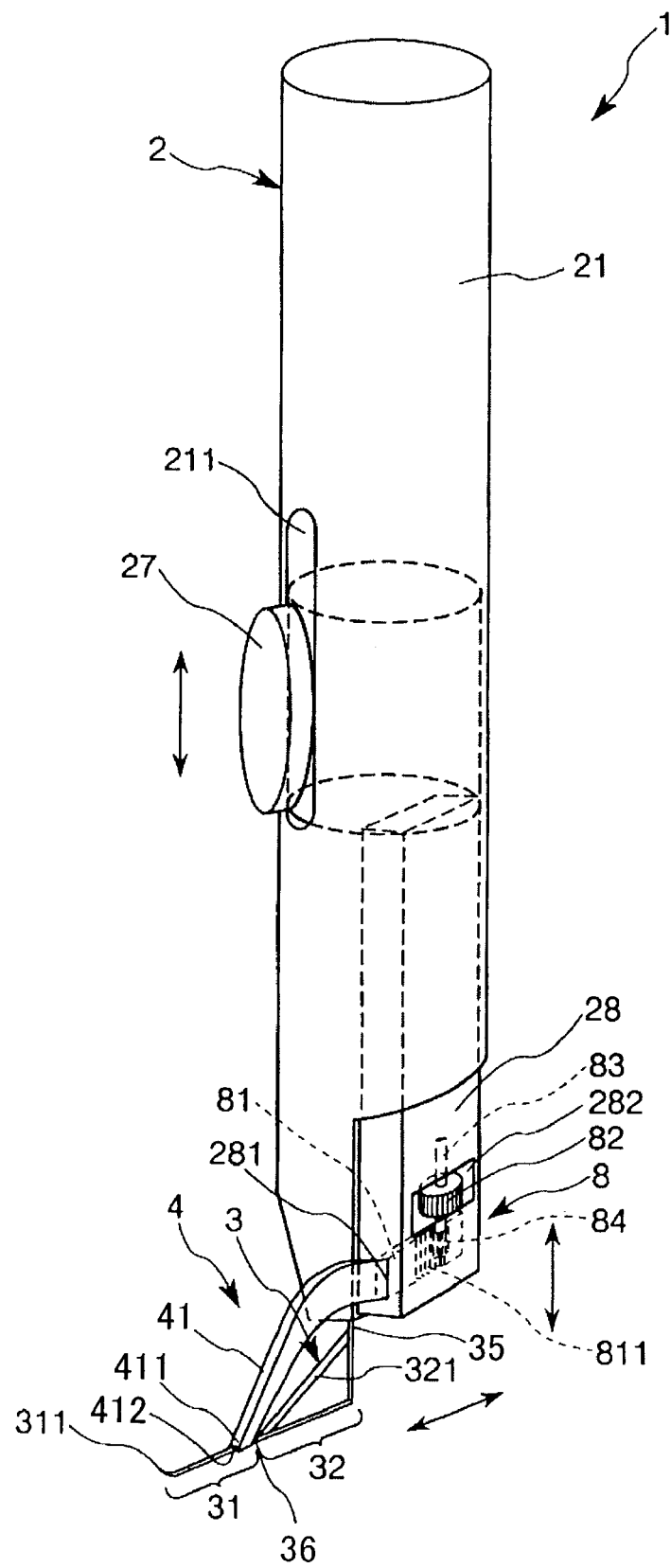
FIG. 15 is a perspective view of a third embodiment of the vascular incision apparatus of the invention.
Figure 16:
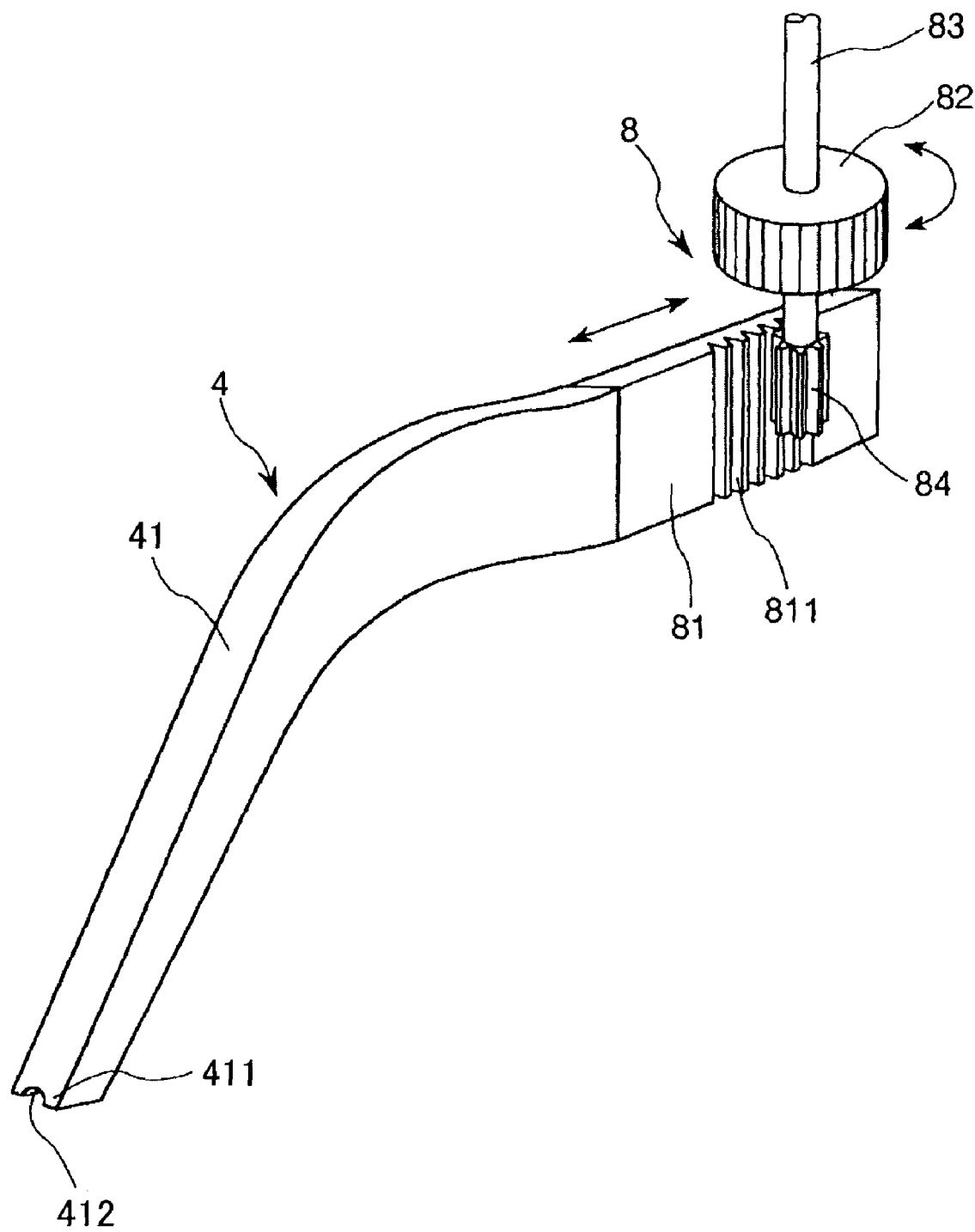
FIG. 16 is a perspective view showing major features of the stopper arm and incision length adjusting mechanism of the apparatus of FIG. 15.

Next, a third embodiment of the vascular incision apparatus of the invention is described. FIG. 15 is a perspective view of a third embodiment of the vascular incision apparatus of the invention. FIG. 16 is a perspective view showing essential features of the stopper arm and incision length adjusting mechanism of the apparatus of FIG. 15.

The third embodiment of the inventive vascular incision apparatus is described below with particular reference to those features which differ from the above-described first embodiment of the invention. Descriptions of like features are omitted. In FIG. 15, the puncturing and cutting member side of the vascular incision apparatus is referred to as the "bottom end" or "bottom," and the body side of the apparatus is referred to as the "top end" or "top." The left side with respect to the thus-defined "bottom" and "top" of the apparatus is referred to herein as the "distal end," and the right side as the "proximal end." Similarly, in FIG. 16, the pinion side of the incision length adjusting mechanism is referred to as the "bottom end" or "bottom," and the substantially cylindrical control member side of the incision length adjusting mechanism is referred to as the "top end" or "top." The left side with respect to the thus-defined "bottom" and "top" of the apparatus is referred to herein as the "distal end," and the right side as the "proximal end."

As shown in these diagrams, the third embodiment of the vascular incision apparatus 1 of the invention has an incision length adjusting mechanism 8 for adjusting the vascular incision length controlled by the incision length controlling means 4.

The incision length adjusting mechanism 8 adjusts the length of the incision made in the blood vessel by changing the position at which the stop 411 comes to rest against the puncturing and cutting member 3 when the stopper arm 41 is in the first position. This is described more fully below.

The body 2 of the vascular incision apparatus has a handle 21 which is hollow on the bottom side thereof. An attachment section 28 is provided within the hollow portion of the handle 21 so as to be vertically movable with respect to the handle 21. The puncturing and cutting member 3 is fixedly attached to the bottom end of the handle 21 with a support 35.

The handle 21 has formed, at the center in the lengthwise direction thereof, a slot 211 which extends lengthwise along part of the handle 21, passes through a wall of the handle 21, and communicates with the hollow portion of the handle 21.

A control member 27 is provided at the top end of the attachment section 28 such as to protrude outward through the slot 211.

An aperture 281 and a recess 282 are formed at the bottom end of the attachment section. The aperture 281 is situated below the recess 282.

The incision length adjusting mechanism 8 includes a slider 81 of substantially rectangular shape positioned at the proximal end of the stopper arm 41, which slider 81 is movable in the lengthwise direction of the needle 31 on the puncturing and cutting member 3.

In this arrangement, the aperture 281 functions as a holder for holding the stopper arm 41 movably in the lengthwise direction of the needle 31 on the puncturing and cutting member 3.

The stopper arm 41 is positioned above the puncturing and cutting member 3, and curves downward from a proximal end to a distal end thereof such as to enable the stop 411 to come to rest against the puncturing and cutting member 3.

The incision length adjusting mechanism 8 has a substantially cylindrical control member 82, a rotating shaft 83, and a pinion 84. The control member 82 is fixedly attached to the shaft 83 at an intermediate position thereon such as to be concentric therewith. The pinion 84 is fixedly attached to a bottom end of the shaft 83 such as to be concentric therewith.

Control member 82 and the pinion 84 are positioned at the bottom end of the attachment section 28 and are rotatable in both the forward and reverse directions (clockwise and counterclockwise directions) about the axis 83. Control member 82 is situated within the recess 282, with a portion thereof protruding outward from the recess 282.

Control member 82 has a peripheral surface that is textured (has concavo-convex (knurling)) to prevent slippage when manipulated (turned).

The slider 81 has formed, on a side thereof that faces the pinion 84, a rack 811 which meshes with the pinion 84.

Operation of the incision length adjusting mechanism 8 in this embodiment of the inventive vascular incision apparatus 1 to adjust the vascular incision length controlled by the incision length controlling means 4 is now described.

When control member 82 is rotated in the counterclockwise direction in FIGS. 15 and 16, the pinion 84 and rack 811 convert this rotation into linear motion by the slider 81 and stopper arm 41, causing the stopper arm 41 to move distally in the lengthwise direction of the needle 31 on the puncturing and cutting member 3.

Conversely, when the control member 82 is rotated in the clockwise direction in FIGS. 15 and 16, the pinion 84 and rack 811 convert this rotation into linear motion by the slider 81 and stopper arm 41, causing the stopper arm 41 to move proximally in the lengthwise direction of the needle 31 on the puncturing and cutting member 3. During such proximal movement, the stopper arm 41 and the slider 81 travel until the stop 411 on the stopper arm 41 reaches the boundary 36, at which point the proximal end of the slider 81 comes to rest against the inner proximal wall of the aperture 281, preventing the stop 411 from moving proximal to the boundary 36.

After rotating the control member 82 to set the stopper arm 41 in the first position, the user can change the position at which the stop 411 comes to rest against the puncturing and cutting member 3 and thereby adjust the vascular incision length controlled by the stopper arm 41.

Shifting control member 27 upward causes the stopper arm 41 to move upward together with the attachment section 28, resulting in separation of the stop 411 on the stopper arm 41, and thus the groove 412 on the stop 411, away from the boundary 36 or the needle 31.

When the stopper arm 41 is in this state (second position), the stop 411 separates from the boundary 36 or needle 31, making it possible for the cutter 32 to cut the blood vessel.

Next, shifting control member 27 downward causes the stopper arm 41 to move downward together with the attachment section 28, causing the stop 411 on the stopper arm 41, and thus the groove 412 on the stop 411, to engage the boundary 36 or needle 31, thus returning the stopper arm 41 to the first position.

When the stopper arm 41 is in this state (first position), the stop 411 is at rest against the boundary 36 or the needle 31, thereby restricting the length of penetration by the needle 31 into the blood vessel and preventing the cutter from cutting the blood vessel.

The advantageous effects provided by this vascular incision apparatus 1 are similar to the effects achievable with the first embodiment of the inventive apparatus described above.

Moreover, the incision length adjusting mechanism 8 in this apparatus 1 enables the length of the incision made in the blood vessel to be easily, rapidly and reliably set to a desired length.

In this third embodiment, as in the first embodiment described above, there may be provided a restoring means which returns the stopper arm 41 to the first position. In addition, as in the second embodiment described above, the stopper arm 41 may be made rotatable with respect to the body 2. Other variations and modifications of the type discussed above in connection with the first embodiment may similarly be applied here.

Figure 17:
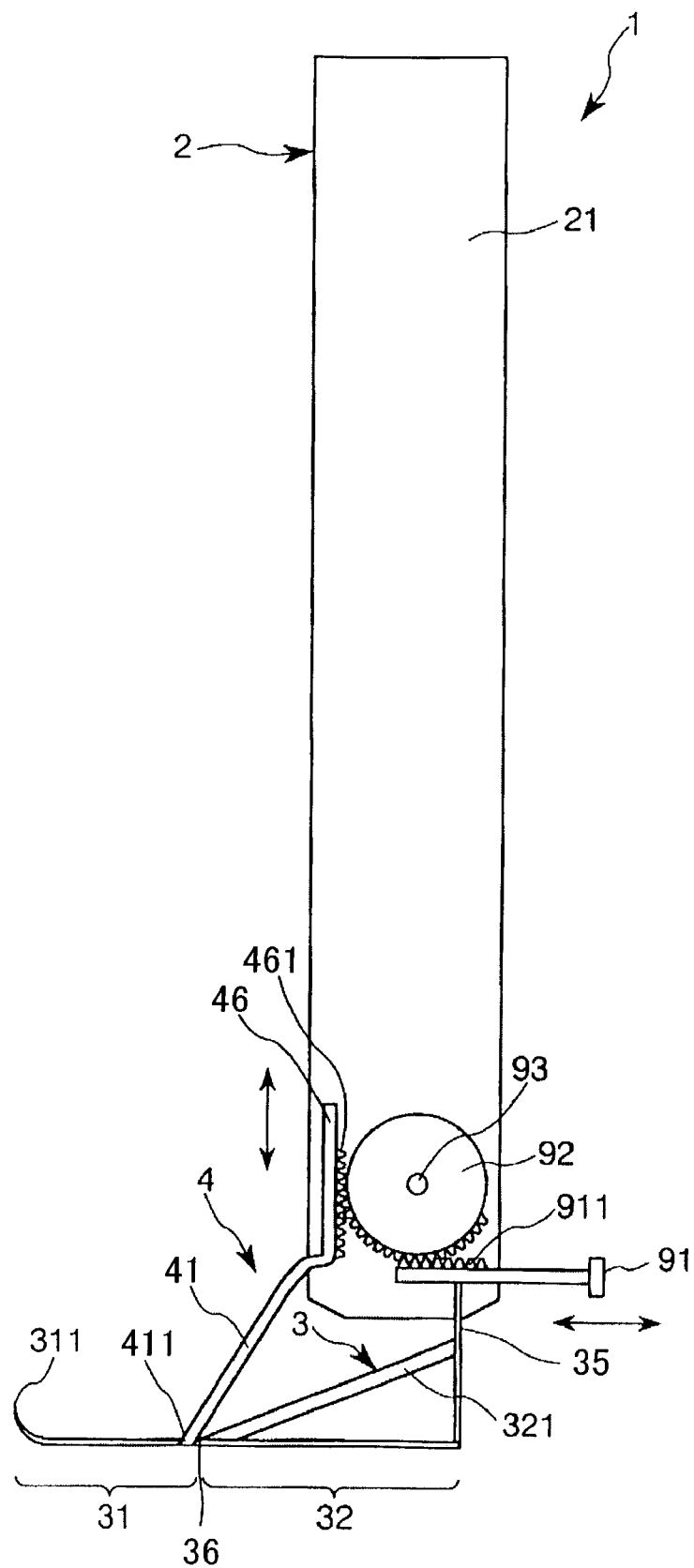
FIG. 17 is a side view, in cross section, of a fourth embodiment of the vascular incision apparatus of the invention.
Figure 18:
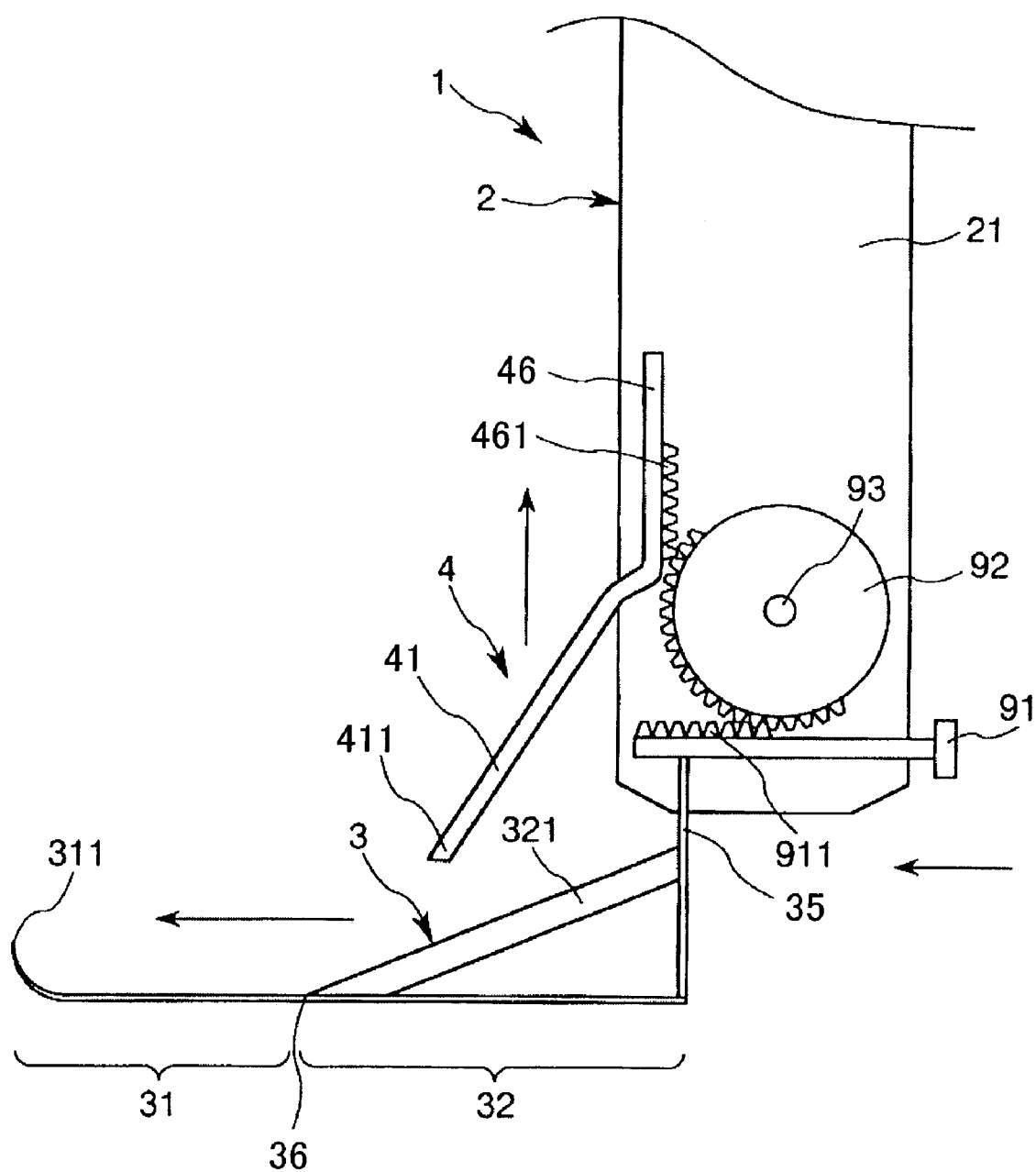
FIG. 18 is a side view, in cross section, showing the apparatus of FIG. 17 after the puncturing and cutting member has been moved.

Next, a fourth embodiment of the vascular incision apparatus of the invention is described. FIG. 17 is a side view, in cross section, of a fourth embodiment of the vascular incision apparatus of the invention. FIG. 18 is a side view, in cross section, showing the apparatus of FIG. 17 after the puncturing and cutting member has been moved.

The fourth embodiment of the inventive vascular incision apparatus is described below with particular reference to those features which differ from the above-described first embodiment of the invention. Descriptions of like features are omitted. In FIGS. 17 and 18, the puncturing and cutting member side of the vascular incision apparatus is referred to as the "bottom end" or "bottom," and the body side of the apparatus is referred to as the top end" or "top." The left side with respect to the thus-defined "bottom" and "top" of the apparatus is referred to herein as the "distal end," and the right side as the "proximal end."

As shown in these diagrams, in the fourth embodiment of the vascular incision apparatus 1 of the invention, the puncturing and cutting member 3 is movable with respect to the body 2. Moreover, this apparatus 1 has a control member 91 for moving the puncturing and cutting member 3, and is configured so that movement (change of position) by the stopper arm 41 is coupled to movement by the puncturing and cutting member 3. This arrangement is described more fully below.

The control member 91 for moving the puncturing and cutting member 3 is provided at the bottom end of the vascular incision apparatus 1, and hence the bottom end of the handle 21, such as to be movable in the lengthwise direction of the needle 31 on the puncturing and cutting member 3. The puncturing and cutting member 3 is fixedly attached to the bottom side of the control member 91 with a support 35. The control member 91 has a rack 911 formed on the top side thereof.

The stopper arm 41 has a plate-like slider 46 at a proximal end (top end) thereof. The slider 46 is provided such as to be vertically movable at the bottom end of the body 2, and thus the bottom end of the handle 21, on the vascular incision apparatus 1. The slider 46 has a rack 461 formed on a proximal end side thereof.

A gear 92 which meshes with racks 911 and 461 is provided at the bottom end of the body 2 on the vascular incision apparatus 1, and thus the bottom end of the handle 21, such as to be rotatable in both the forward and reverse directions (clockwise and counterclockwise directions) about a rotating shaft 93.

The operation of this embodiment of the inventive vascular incision apparatus 1 is now described.

Referring to FIG. 18, moving control member 91 by pushing it distally causes the puncturing and cutting member 3 to move distally together with the control member 91.

At the same time, this linear motion by control member 91 is converted by the rack 911 and the gear 92 into rotation by the gear 92. Rotation by the gear 92 is in turn converted by the gear 92 and the rack 461 into linear motion by the slider 46 and the stopper arm 41, causing the stopper arm 41 to move upward. This upward movement separates the stop 411 on the stopper arm 41, and thus the groove 412 on the stop 411, from the boundary 36, placing the stopper arm 41 in the second position.

As shown in FIG. 18, subsequent distal movement by the puncturing and cutting member 3 causes the blade 321 on the cutter 32 to cut the blood vessel.

Referring next to FIG. 17, moving the control member 91 by pulling it proximally causes the puncturing and cutting member 3 to move proximally together with the control member 91.

At the same time, this linear motion by control member 91 is converted by the rack 911 and gear 92 into rotation by the gear 92. Rotation by the gear 92 is in turn converted by the gear 92 and the rack 461 into linear motion by the slider 46 and the stopper arm 41, causing the stopper arm 41 to move downward. This downward movement brings the stop 411 on the stopper arm 41 up against the boundary 36, causing the groove 412 on the stop 411 to engage with the boundary 36, thus placing the stopper arm 41 in the first position.

In the state shown in FIG. 17 (stopper arm 41 in first position), the stop 411 rests against the boundary 36, restricting the length of penetration by the needle 31 into the blood vessel and preventing the cutter 32 from cutting the blood vessel.

When the puncturing and cutting member 3 is moved proximally, it travels until the stop 411 on the stopper arm 41 reaches the boundary 36, beyond which further proximal movement is prevented.

The advantageous effects provided by this vascular incision apparatus 1 are similar to the effects achievable with the first embodiment of the inventive apparatus described above.

With this vascular incision apparatus 1, an incision can be created in a blood vessel by manipulating the control member 91 to effect movement of the puncturing and cutting member 3 without having to move the body 2. In particular, movement by the stopper arm 41 is coupled to movement by the puncturing and cutting member 3, thus enabling an incision to be created in a blood vessel even more easily and rapidly than possible with the apparatus according to the first embodiment of the invention.

According to one variation of this fourth embodiment, the puncturing and cutting member 3 and the stopper arm 41 are manipulated separately rather than coupling movement by the puncturing and cutting member 3 with movement (change of position) by the stopper arm 41.

As in the first embodiment described above, this fourth embodiment of the inventive apparatus may be provided with a restoring means which returns the stopper arm 41 to the first position. As in the second embodiment described above, the stopper arm 41 may be made rotatable with respect to the body 2. As in the third embodiment described above, an incision length adjusting mechanism which adjusts the vascular incision length controlled by the incision length controlling means 4 may also be provided. Other variations and modifications of the type discussed above in connection with the first embodiment may similarly be applied here.

Figure 19:
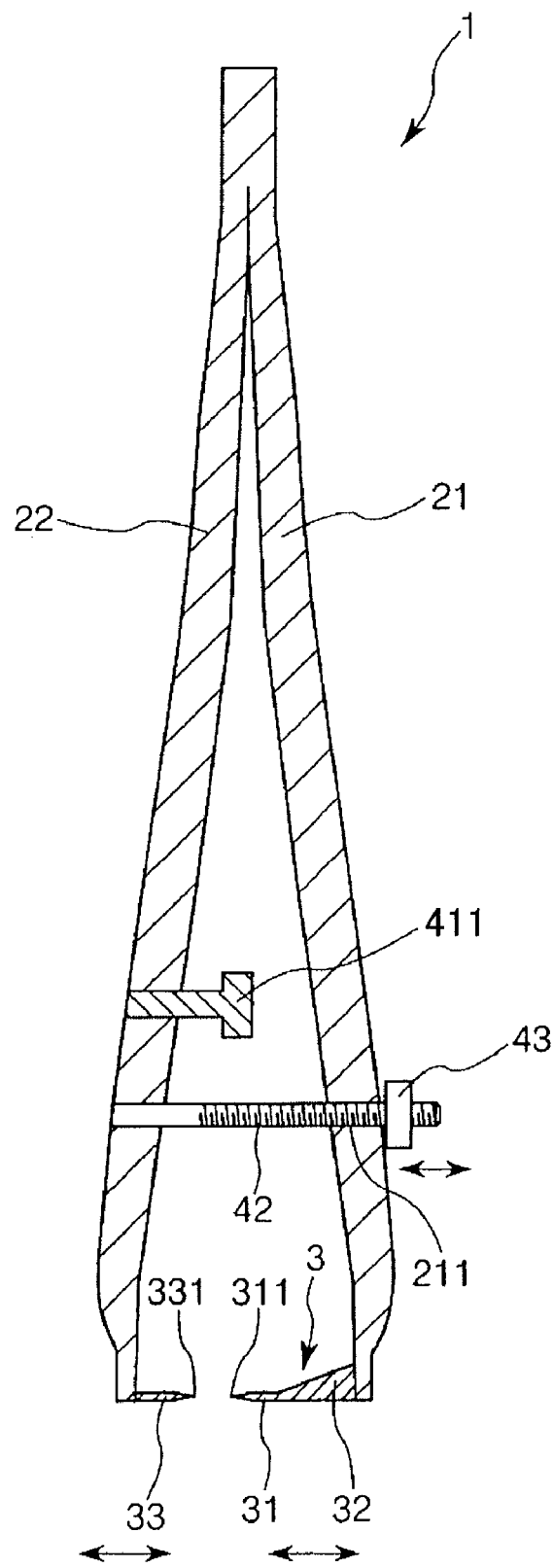
FIG. 19 is a cross-sectional view of a fifth embodiment of the vascular incision apparatus of the invention.
Figure 20:
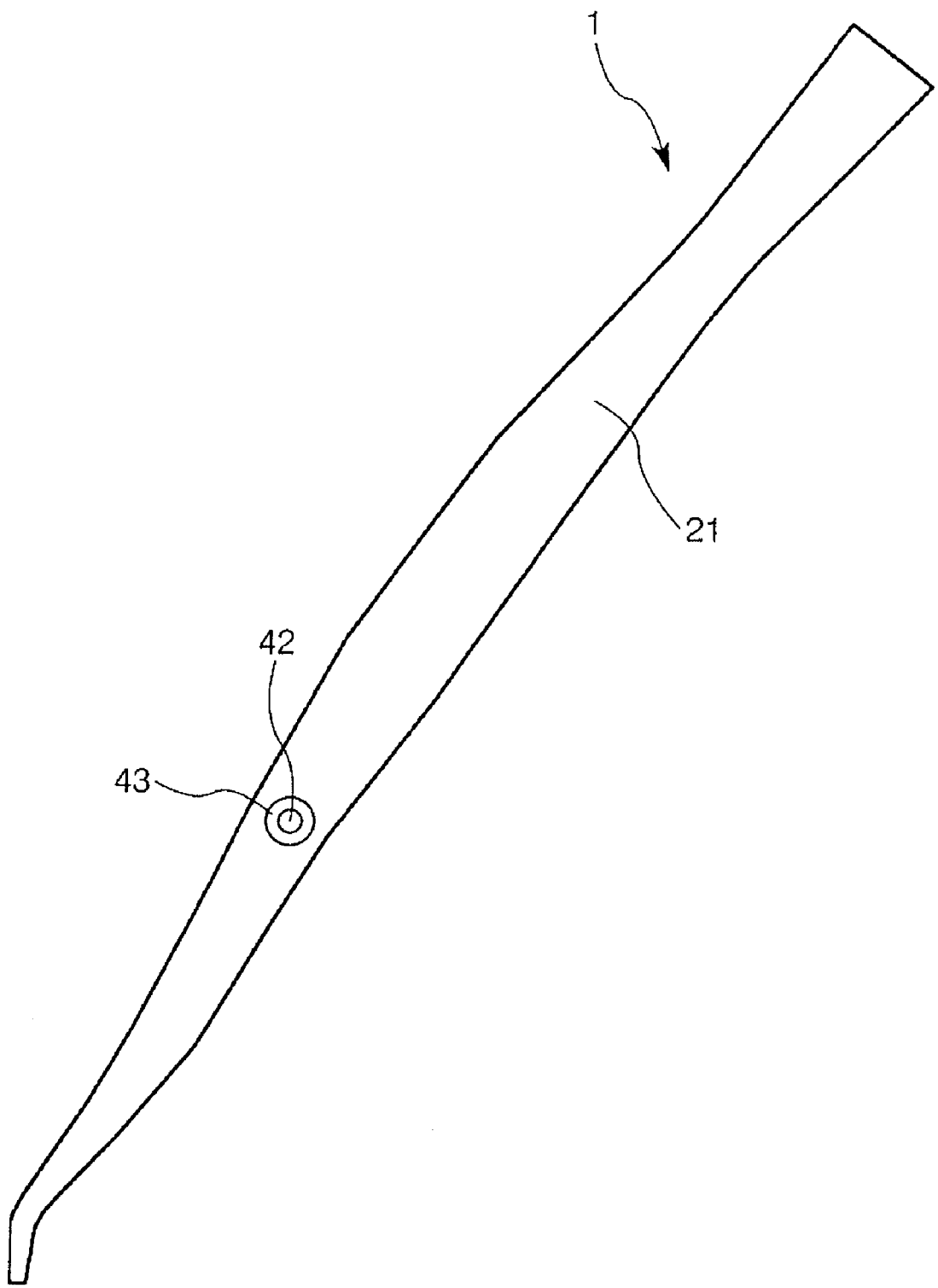
FIG. 20 is a side view of the apparatus of FIG. 19.

Next, a fifth embodiment of the vascular incision apparatus of the invention is closely described while referring to the attached diagrams. FIG. 19 is a cross-sectional view of a fifth embodiment of the vascular incision apparatus of the invention, FIG. 20 is a side view of the apparatus of FIG. 19 (as seen from the right side), FIG. 21 is a front view of the bottom of the apparatus of FIG. 19, and FIG. 22 is another cross-sectional view of the apparatus of FIG. 19.

Figure 21:
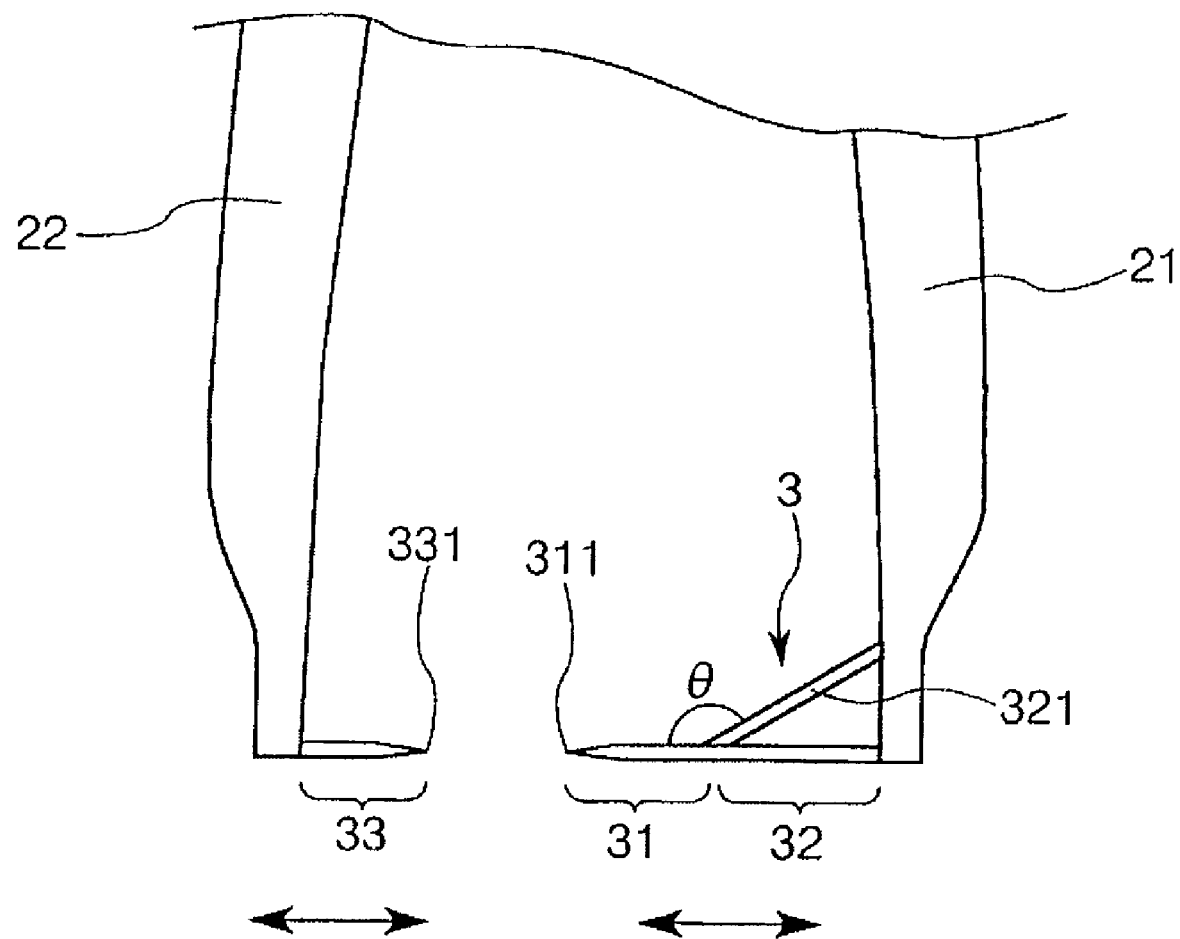
FIG. 21 a front view of the bottom of the apparatus of FIG. 19.
Figure 22:
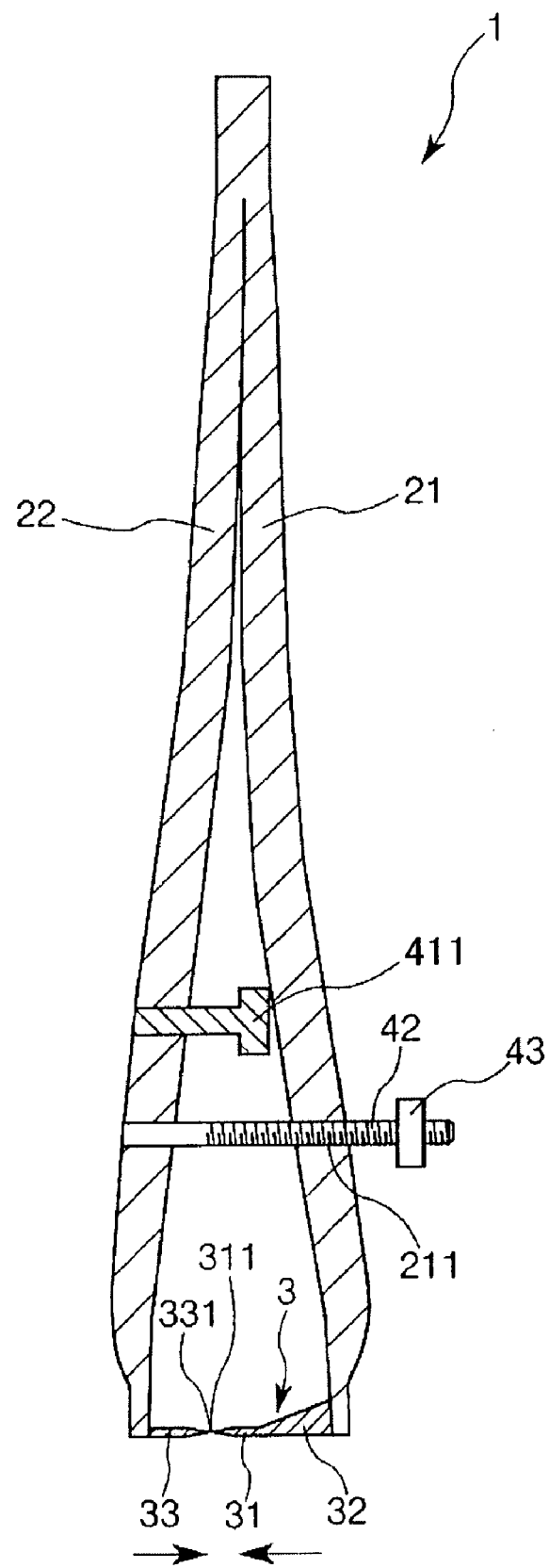
FIG. 22 is another cross-sectional view of the apparatus of FIG. 19.

In FIGS. 19, 21 and 22, the side of the vascular incision apparatus 1 on which the puncturing and cutting member is provided on a pair of handles is referred to as the "bottom end" or "bottom," and the side where the pair of handles are joined to each other is referred as the "top end" or "top."

The vascular incision apparatus 1 shown in these diagrams is an instrument for creating an incision in a blood vessel. The apparatus 1 has a pair of elongated handles 21 and 22 which are joined (fixedly attached) to each other at the top end thereof.

This pair of handles 21, 22 has an elasticity that enables the bottom end of the first handle 21 and the bottom end of the second handle 22 to move apart and together. This induces one of the subsequently described first and second needles 31, 33 to move relative to the other, causing a needle point 311 on the first needle 31 and a needle point 331 on the second needle to move apart and to move together or touch.

The pair of handles 21, 22 are urged, under the elastic force (restoring force) thereof, in a direction that mutually separates the bottom end of the first handle 21 and the bottom end of the second handle 22 (a direction that mutually separates the point 311 on the first needle 31 and the point 331 on the second needle 33).

The user uses the vascular incision apparatus 1 by holding and manipulating this pair of handles 21, 22 with the hand and fingers.

That is, in the fifth embodiment of the vascular incision apparatus of the invention, this pair of handles 21 and 22 serves both as an urging means and a control means.

The first handle 21 has, joined at the bottom end thereof, a puncturing and cutting member 3 composed of a first needle 31 with a sharp point 311 on a distal end thereof for penetrating the blood vessel and a cutter 32 on a proximal end side of the first needle 31 for making an incision in the blood vessel.

The cutter 32 is substantially triangular in side shape. The blade 321 is formed on the top of the cutter 32. In another arrangement, the cutter 32 may be composed of a section which is an extension of the needle 31 and a blade 321 formed on the top side of the extension. In this arrangement, the extension and the blade 321 are joined together at the distal ends thereof, and the extension and the blade 321 are separately joined at their respective proximal ends to the bottom end of the first handle 21, giving the cutter 32 a substantially triangular shape.

The second handle 22 has joined at the bottom end thereof a second needle 33 for penetrating the blood vessel, which second needle 33 has a sharp point (distal end) 331 which faces the point 311 of the first needle 31 across a predetermined distance.

The puncturing and cutting member 3 and the second needle 33 are the major features of the puncturing and cutting means in this embodiment of the inventive vascular incision apparatus 1.

The angle θ (in degrees) formed between the first needle 31 and the blade 321 on the cutter 32 in the vicinity of a boundary between the needle 31 and the cutter 32, while not subject to any particular limitation, is preferably not more than 180°, and more preferably about 120 to 180°. A vascular incision can be more easily created at an angle θ of not more than 180°.

The needles 31 and 33 and the cutter 32 have respective lengths which are not subject to any particular limitation and may be suitably set according to various conditions, such as the length of the vascular incision to be made.

In the present embodiment of the invention, the puncturing and cutting member 3 (composed of first needle 31 and cutter 32) and the second needle 33 may be provided detachably on the first and second handles 21 and 22. That is, the puncturing and cutting member 3 and the second needle 33 may be replaceable.

As shown in FIG. 19, a stop (closest approach state controlling means) 411 and a bolt (the threaded portion of a bolt) 42 are each provided on the first handle 21 side of the second handle 22.

The bolt 42 is passed through a through-hole 211 formed in the first handle 21 at a position corresponding to the bolt 42, and a nut 43 is screwed onto the bolt 42 from the right side of the first handle 21 in FIG. 19.

As noted above, the pair of handles 21 and 22 are urged, under the elastic force thereof, in a direction that mutually separates the bottom end of the first handle 21 and the bottom end of the second handle 22, bringing the first handle 21 up against the nut 43. The nut 43 holds the first needle 31 and the second needle 33 in a "maximum separation state" in which they are most widely separated.

In this maximum separation state, the distance between the point 311 on the first needle 31 and the point 331 on the second needle 33 is at a maximum. This maximum distance is substantially the length of the incision to be formed in the blood vessel by the cutter 32.

Turning the nut 43 moves it along the bolt 42 in the left-right direction in FIG. 19, changing the maximum separation state, and thus the maximum distance, between the point 311 on the first needle 31 and the point 331 on the second needle 33.

Moving the nut 43 leftward in FIG. 19 decreases the maximum distance, resulting in a shorter incision length. Conversely, moving the nut 43 rightward in FIG. 19 increases the maximum distance, resulting in a longer incision length.

Accordingly, the bolt 42 and the nut 43 together comprise a maximum separation state controlling means for controlling the maximum separation state between the first needle 31 and the second needle 33, as well as an incision length adjusting mechanism for adjusting the maximum distance between the point 311 on the first needle 31 and the point 331 on the second needle 33.

As shown in FIG. 22, when the user squeezes the pair of handles 21, 22, the puncturing and cutting member 3 (composed of first needle 31 and cutter 32) and the second needle 33 move in directions that bring the point 311 on the first needle 31 and the point 331 on the second needle 33 closer together. Eventually, the first handle 21 reaches the stop 411, at which point the first needle 31 and the second needle 33 are in their closest approach state.

The vascular incision apparatus 1 according to the present embodiment of the invention is constructed so that, in the closest approach state, the point 311 on the first needle 31 and the point 331 on the second needle 33 are exactly touching or separated by only a very small distance.

The stop 411 helps prevent damage to the point 311 on the first needle 31 and the point 331 on the second needle 33.

Moreover, by constructing the apparatus 1 so that, in the closest approach state, the point 311 on the first needle 31 and the point 331 on the second needle 33 are exactly touching or separated by only a very small distance, the step of forming an incision in the blood vessel with the cutter 32 can be carried out smoothly and reliably.

The first needle 31 and the second needle 33 may be made of any suitable material, examples of which include various metals (e.g., stainless steel, titanium, steel, iron, and alloys thereof) and ceramics.

The cutter 32 too may be made of any suitable material, examples of which include various metals (e.g., stainless steel, titanium, steel, iron, and alloys thereof) and ceramics.

The pair of handles 21, 22 may likewise be made of any suitable material, examples of which include various metals (e.g., stainless steel, titanium, steel, iron, and alloys thereof) and plastics (polypropylene, polyethylene, polycarbonate, nylon and the like).

In this fifth embodiment of the vascular incision apparatus of the invention, as in the first embodiment described above, the first needle 31 and the cutter 32 have an integral construction which may be arrived at either by integrally forming the needle 31 and the cutter 32, or by separately forming then uniting the needle 31 and the cutter 32.

In the present embodiment, the cutter is provided on the first needle 31 side, although an alternative arrangement in which it is provided on the second needle 33 side is also acceptable.

In this embodiment, the puncturing and cutting member 3 (composed of first needle 31 and cutter 32) and the second needle 33 are fixedly attached to the respective handles 21, 22. However, as noted above in connection with the first embodiment of the vascular incision apparatus 1 of the invention, it is often advantageous for the puncturing and cutting member 3 (composed of first needle 31 and cutter 32) and the second needle 33 to be freely detachable from the respective handles 21 and 22, and thus replaceable.

Should the puncturing and cutting member 3 or the needle 33 undergo breakage, damage or deterioration, such an arrangement would allow replacement of the puncturing and cutting member 3 or the needle 33 alone, resulting in lower user costs than if the entire apparatus 1 had to be replaced.

Moreover, even if the apparatus 1 does not include an incision length adjusting mechanism, the vascular incision may be set to the desired length by having on hand at the point of use a plurality of such puncturing and cutting members 3 with first needles 31 of varying length and a plurality of second needles 33 of varying length, and selecting and mounting the most appropriate puncturing and cutting member 3 and second needle 33 from among these.

The shapes of the first needle 31 and cutter 32 on the puncturing and cutting member 3 and the shape of the second needle 33 are not limited to the shapes shown in the accompanying diagrams. Examples of other suitable needle configurations are described below.

Figure 30:
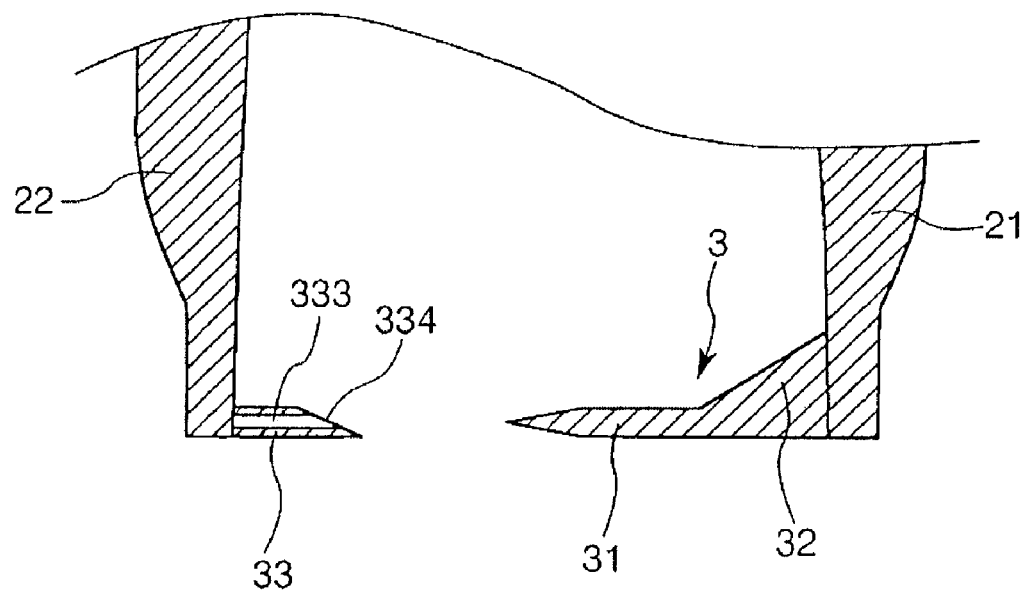
FIGS. 30 and 31 are cross-sectional views of a further configuration of the needles in the inventive apparatus, with the elements shown respectively in a mutually separated and a mutually proximate relationship.
Figure 31:
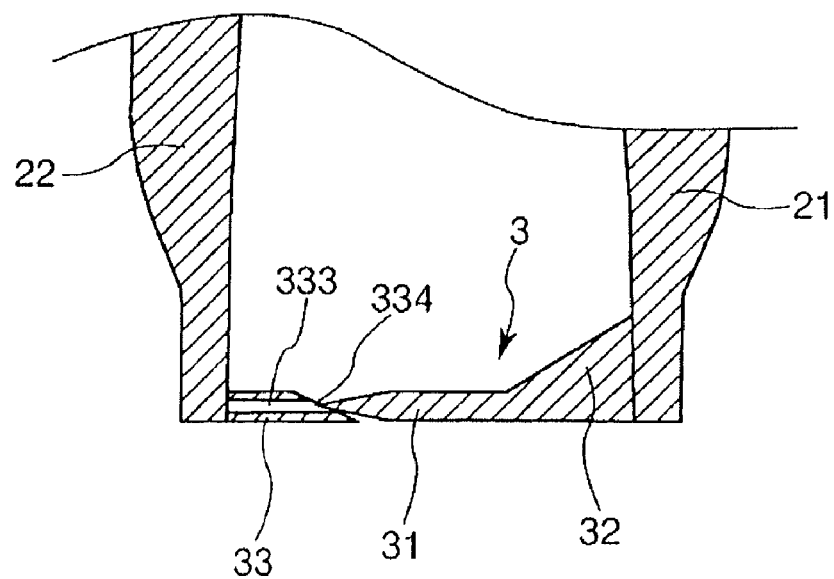
Figure 32:
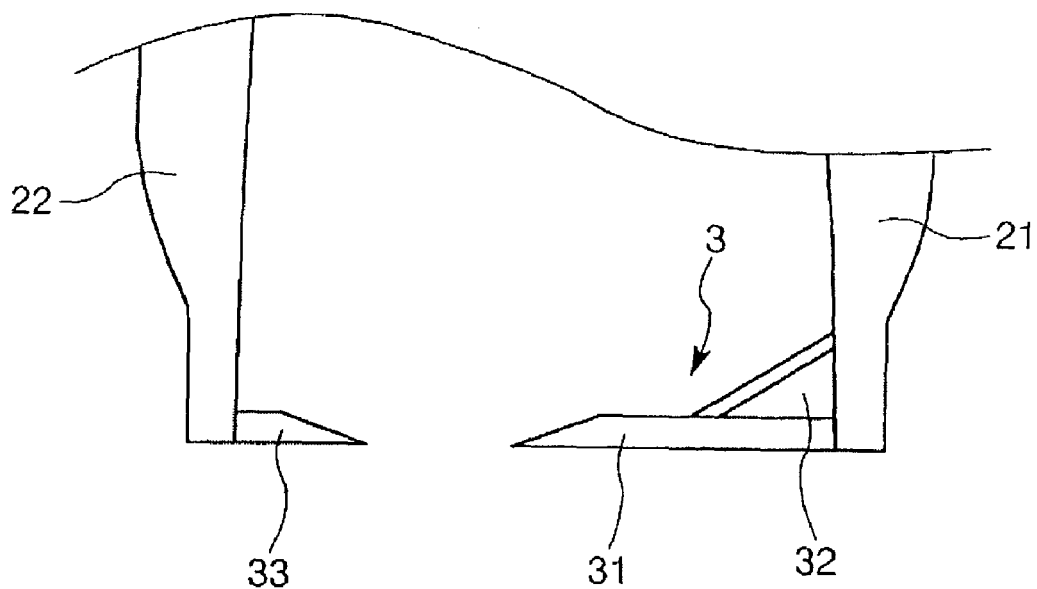
FIGS. 32 and 33 are side views of a still further configuration of the needles in the inventive apparatus, with the elements shown respectively in a mutually separated and a mutually proximate relationship.
Figure 33:
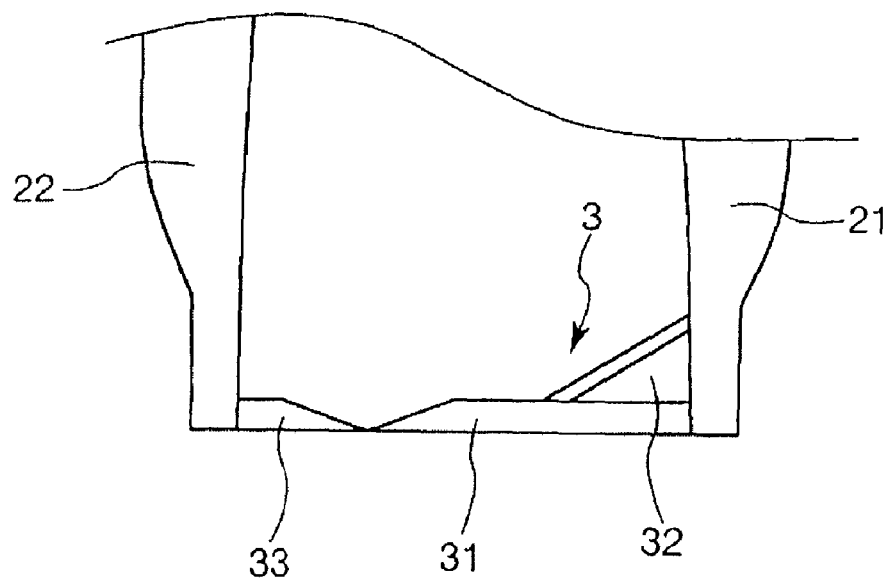

FIGS. 26 to 31 are cross-sectional views of other configurations of the needles, and FIGS. 32 and 33 are side views of yet another configuration of the needles.

Figure 26:
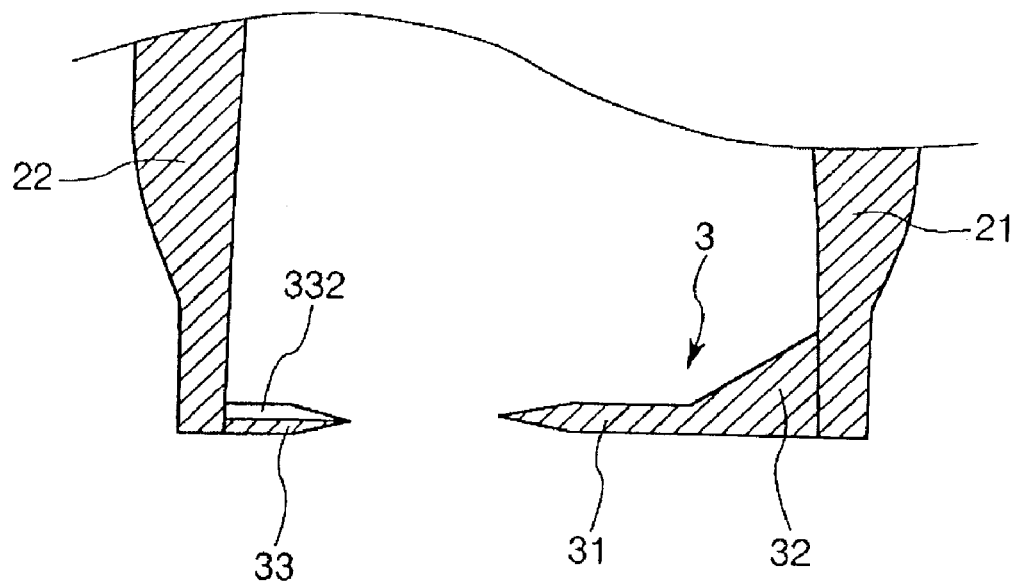
FIGS. 26 and 27 are cross-sectional views of another configuration of the needles in the fifth embodiment of the inventive apparatus, with the needles shown respectively in a mutually separated and a mutually proximate relationship.

In the configuration shown in FIG. 26, the second needle 33 has formed at the distal end thereof a groove 332 which engages the distal end of the first needle 31.

Figure 27:
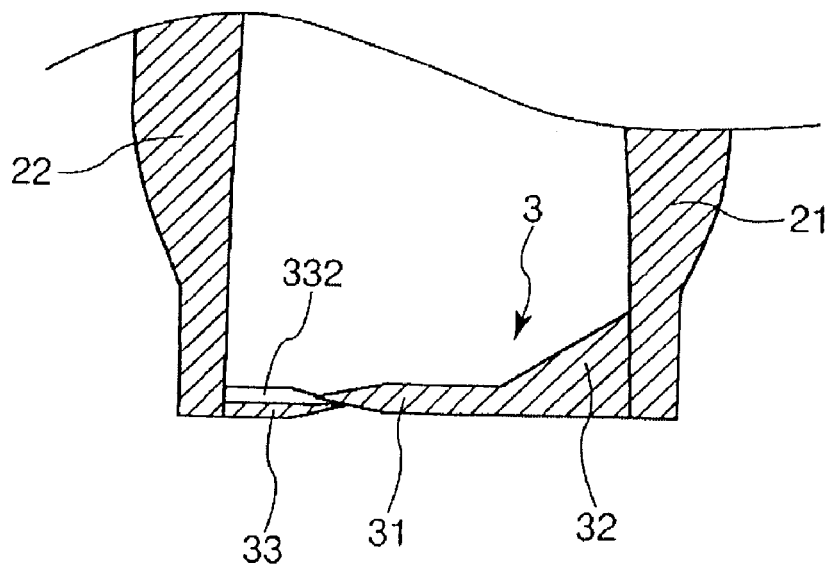

Referring to FIG. 27, when the user squeezes the pair of handles 21, 22, the puncturing and cutting member 3 and the second needle 33 move in directions that bring the point 311 on the first needle 31 and the point 331 on the second needle 33 closer together. The distal end of the first needle 31 then engages the groove 332 of the second needle 33. At the same time, first handle 21 reaches stop 411, resulting in a closest approach state.

This arrangement makes it possible to easily and reliably bring the point 311 of the first needle 31 and the point 331 of the second needle 33 into mutual contact while preventing any damage to the respective points 311 and 331.

In the illustrated example, the groove 332 extends along the entire length of the second needle 33. However, in a variation of the foregoing configuration, the groove 332 may be provided only at the distal end of the second needle 33.

Conversely, in another variation, a groove which engages the distal end of the second needle 33 may be formed at the distal end of the first needle 31.

Figure 28:
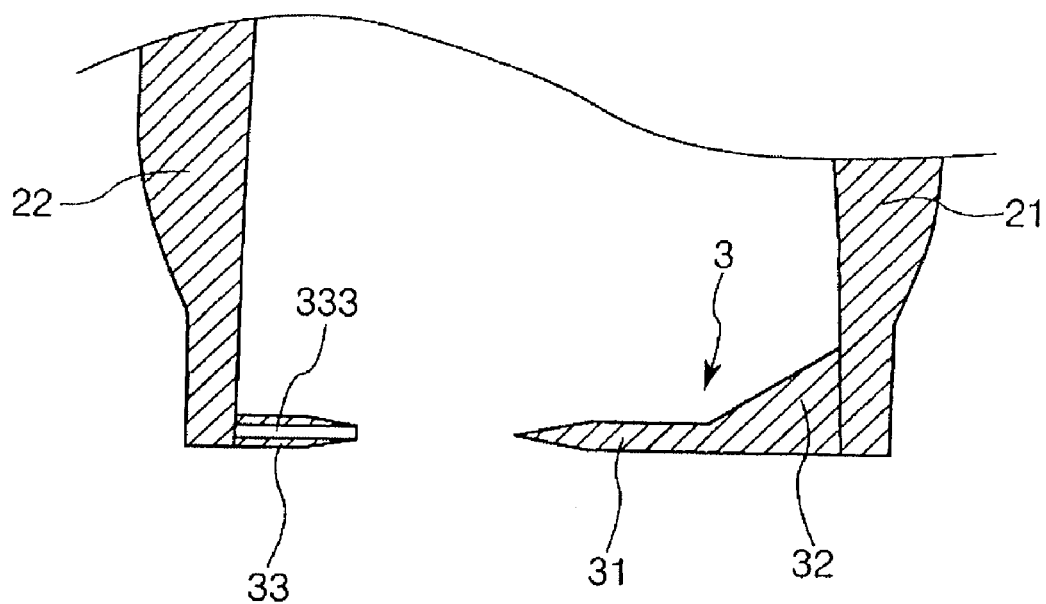
FIGS. 28 and 29 are cross-sectional views of yet another configuration of the needles in the same embodiment of the apparatus, with the elements shown respectively in a mutually separated and a mutually proximate relationship.

In the configuration shown in FIG. 28, the second needle 33 has formed at the distal end thereof an aperture 333 which receives the distal end of the first needle 31.

Figure 29:
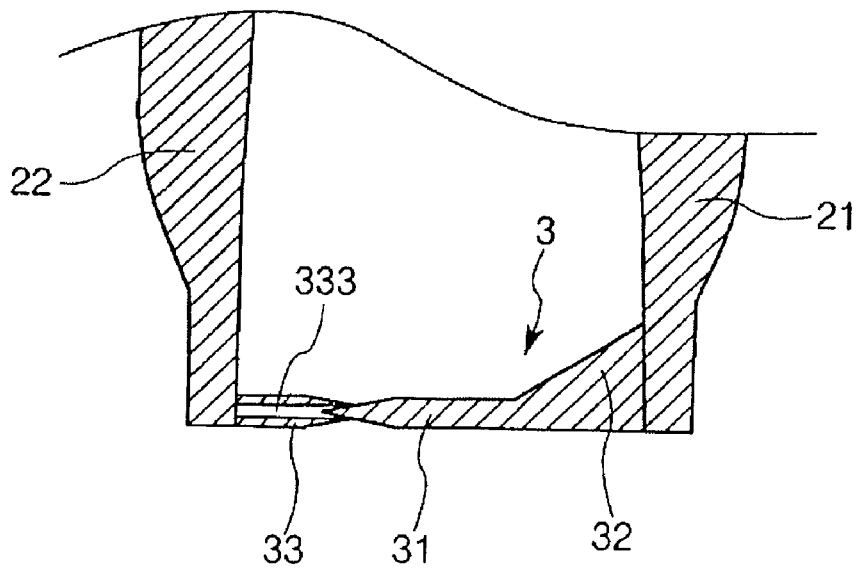

As shown in FIG. 29, when the user squeezes the pair of handles 21, 22, the puncturing and cutting member 3 and the second needle 33 move in directions that bring the point 311 on the first needle 31 and the point 331 on the second needle 33 closer together. The distal end of the first needle 31 is then inserted within the aperture 333. At the same time, first handle 21 reaches stop 411, resulting in a closest approach state.

This arrangement makes it possible to easily and reliably bring the point 311 of the first needle 31 and the point 331 of the second needle 33 into mutual contact while preventing any damage to the respective points 311 and 331.

In the illustrated example, the aperture 333 extends along the entire length of the second needle 33. However, in a variation of the foregoing configuration, the aperture 333 may instead be provided only at the distal end of the second needle 33.

Conversely, in another variation, an aperture which receives the distal end of the second needle 33 may be formed at the distal end of the first needle 31.

In the configuration shown in FIG. 30, the second needle 33 has formed at the distal end thereof an aperture 333 which receives the distal end of the first needle 31. The second needle 33 also has formed at the distal end thereof a beveled face 334 which angles downward toward the distal side.

As shown in FIG. 31, when the user squeezes the pair of handles 21, 22, the puncturing and cutting member 3 and the second needle 33 move in directions that bring the point 311 on the first needle 31 and the point 331 on the second needle 33 closer together. The distal end of the first needle 31 is then inserted within the aperture 333. At the same time, first handle 21 reaches stop 411, resulting in a closest approach state.

This arrangement makes it possible to easily and reliably bring the point 311 of the first needle 31 and the point 331 of the second needle 33 into mutual contact while preventing any damage to the respective points 311 and 331.

In the illustrated example, the aperture 333 extends along the entire length of the second needle 33. However, in a variation of the foregoing configuration, the aperture 333 may instead be provided only at the distal end of the second needle 33.

Conversely, in another variation, an aperture which receives the distal end of the second needle 33 and a beveled face may be formed at the distal end of the first needle 31.

In the configuration shown in FIG. 32, the distal end of the first needle 31 and the distal end of the second needle 33 are both angled downward.

As shown in FIG. 33, when the user squeezes the pair of handles 21, 22, the puncturing and cutting member 3 and the second needle 33 move in directions that bring the point 311 on the first needle 31 and the point 331 on the second needle 33 closer together. When the first handle 21 reaches the stop 411, the closest approach state is achieved.

This arrangement makes it possible to easily and reliably puncture the blood vessel with the first needle 31 and the second needle 33.

In a variation of the foregoing configuration, the distal end of only one of the first and second needles 31, 33 may be angled downward.

In another variation, the needles may be angled downward over their entire respective lengths rather than only at the distal ends.

In the various configurations shown in FIGS. 26 to 31, the distal end of the first needle 31 and the distal end of the second needle 33 may each be angled downward, or the distal end of only one of the first and second needles 31, 33 may be angled downward.

Alternatively, one or both of the needles in any of these configurations may be angled downward over the entire length thereof rather than only at the distal end.

The method of use, or operation, of the vascular incision apparatus 1 according to this embodiment is now described.

Figure 23:
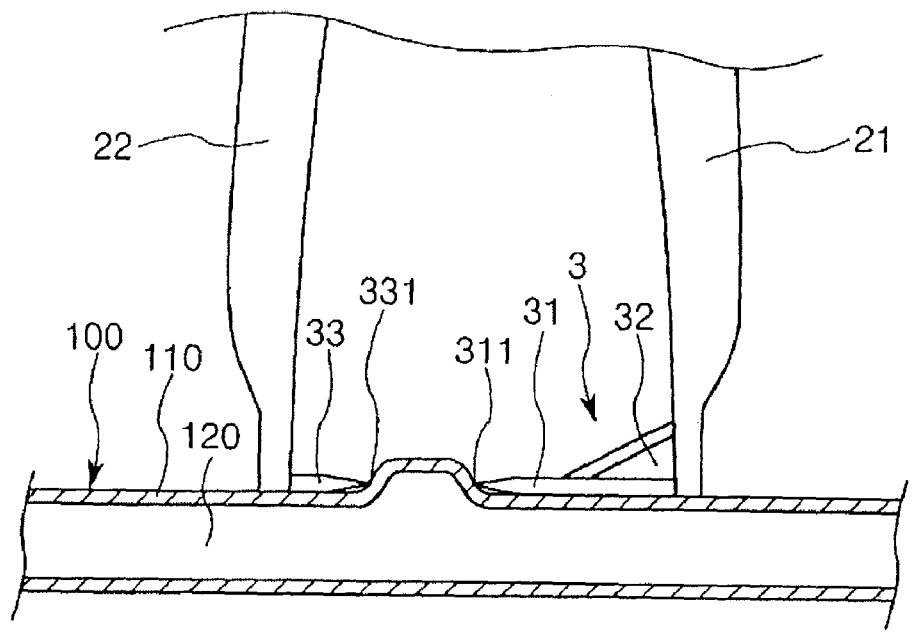
FIGS. 23 to 25 is a sequence of schematic views illustrating how the apparatus of FIG. 19 works.
Figure 24:
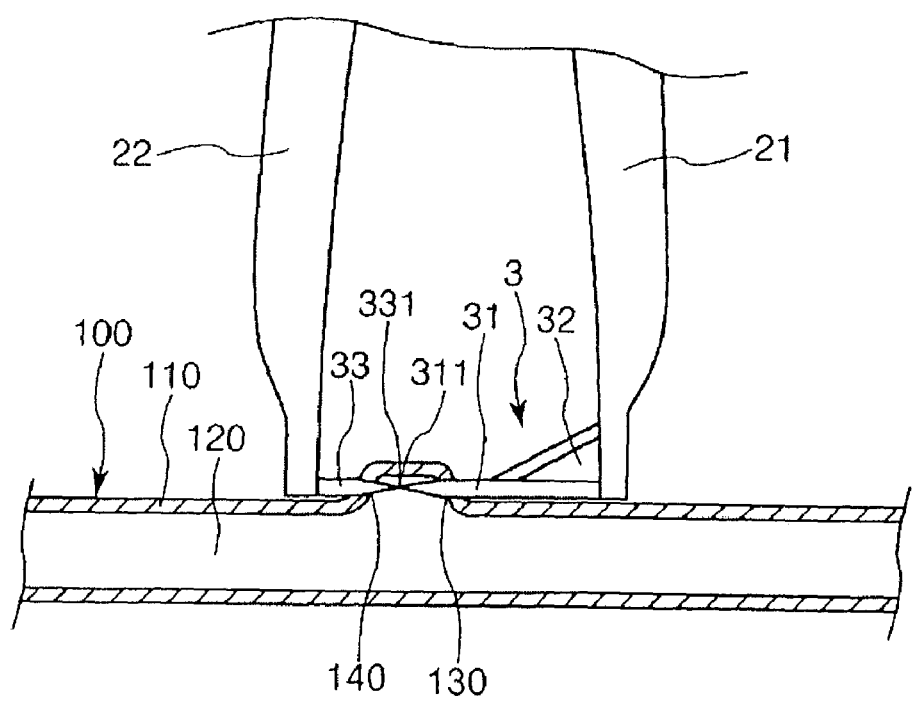
Figure 25:
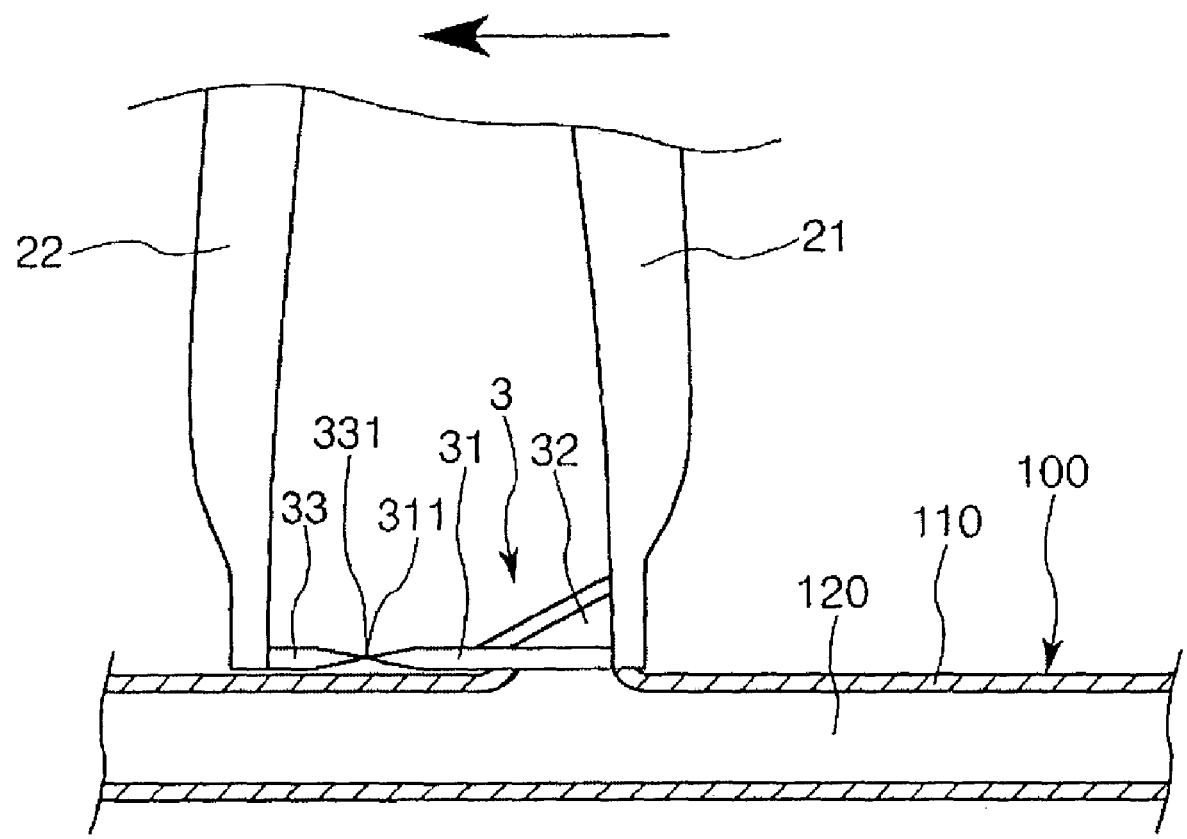

FIGS. 23 to 25 is a sequence of schematic views illustrating how the vascular incision apparatus 1 shown in FIG. 19 works. In FIGS. 23 to 25, the blood vessel 100 side is referred to as the "bottom end" or "bottom," and the apparatus 1 side is referred to as the "top end" or "top."

When an incision is to be created in a blood vessel 100 using the vascular incision apparatus 1, if necessary, the user first turns the nut 43 to adjust the maximum distance between the point 311 on the first needle 31 and the point 331 on the second needle 33 to the desired incision length for the blood vessel 100.

Turning the nut 43 so that it moves leftward in FIG. 19 decreases the maximum distance between the point 311 on the first needle 31 and the point 331 on the second needle 33, shortening the incision length. Conversely, turning the nut 43 so that it moves rightward in FIG. 19 increases the maximum distance, resulting in a larger incision length.

The user then grasps the pair of handles 21, 22 on the apparatus 1 with the hand and fingers and, as shown in FIG. 23, presses the bottom of the incision and cutting member 3 and the second needle 33 against an outer wall 110 of the blood vessel 100.

Next, the pair of handles 21, 22 are squeezed together as shown in FIG. 22. This causes handles 21 and 22 to bend, so that the puncturing and cutting member 3 (composed of first needle 31 and cutter 32) and the second needle 33 move in directions that bring the point 311 on the first needle 31 and the point 331 on the second needle 33 closer together.

When this is done, as shown in FIG. 24, the first needle 31 and the second needle 33 each puncture the wall 110 of the blood vessel 100, with the point 311 on the first needle 31 and the point 331 on the second needle 33 touching or coming into close proximity within the lumen 120 of the blood vessel 100. At the same time, as shown in FIG. 22, the handle 21 reaches the stop 411, by means of which the first needle 31 and the second needle 33 are held in the closest approach state.

The foregoing procedure establishes the site and length of the incision made in the blood vessel 100. That is, the incision site extends between an entry opening 130 created by the first needle 31 in blood vessel 100 and an entry opening 140 created by the second needle 33 in the blood vessel 100. The incision length is the length between the two openings.

Next, as shown in FIG. 25, the user advances the vascular incision apparatus 1 toward the distal side of the first needle 31 (direction of arrow in FIG. 25). As the cutter 32, guided by the first needle 31 and the second needle 33, travels from entry opening 130 to entry opening 140 in the blood vessel 100, the blade 321 on the cutter 32 cuts open the wall 110 of the vessel 100 between openings 130 and 140.

When incision of the blood vessel 100 is complete, the squeezing pressure applied to the pair of handles 21, 22 is eased, whereupon the bottom ends of the handles 21, 22 separate under the elastic forces therein, resulting in separation of the point 311 on the first needle 31 from the point 331 on the second needle 33. The first needle 31 and the second needle 33 attain their most widely separated state when the first handle 21 reaches the nut 43.

The vascular incision apparatus 1 thus controls, by means of the point 311 on the first needle 31 and the point 331 on the second needle 33, the length of the incision created in the blood vessel, resulting in an incision which extends between entry opening 130 and entry opening 140 in the blood vessel 100. This enables the blood vessel to be easily and reliably incised to the desired length.

Also, because the area to be incised is the interval between entry opening 130 and entry opening 140 in the blood vessel 100, the incision can be completed in a single action. This enables a blood vessel to be rapidly incised to the desired length.

Another advantageous feature of this embodiment is the ability to easily and reliably adjust the length of the incision in the blood vessel by turning the nut 43.

Next, a sixth embodiment of the vascular incision apparatus of the invention is described.

Figure 34:
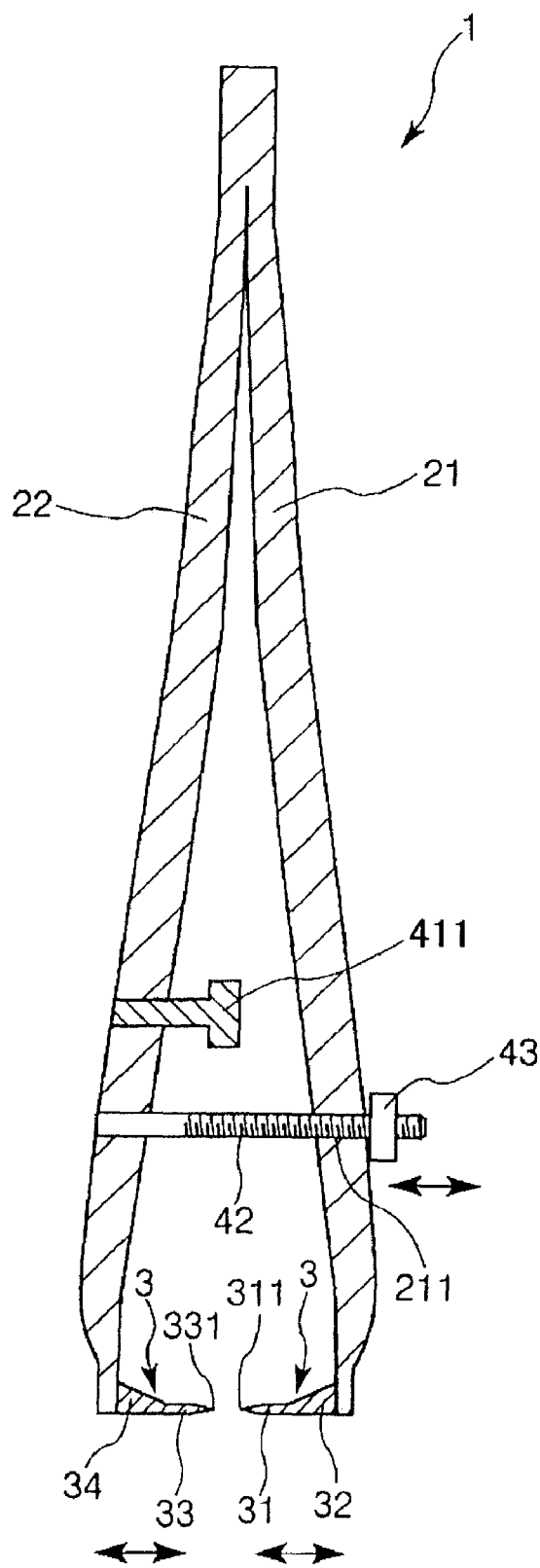
FIG. 34 is a cross-sectional view of a sixth embodiment of the vascular incision apparatus of the invention.
Figure 35:
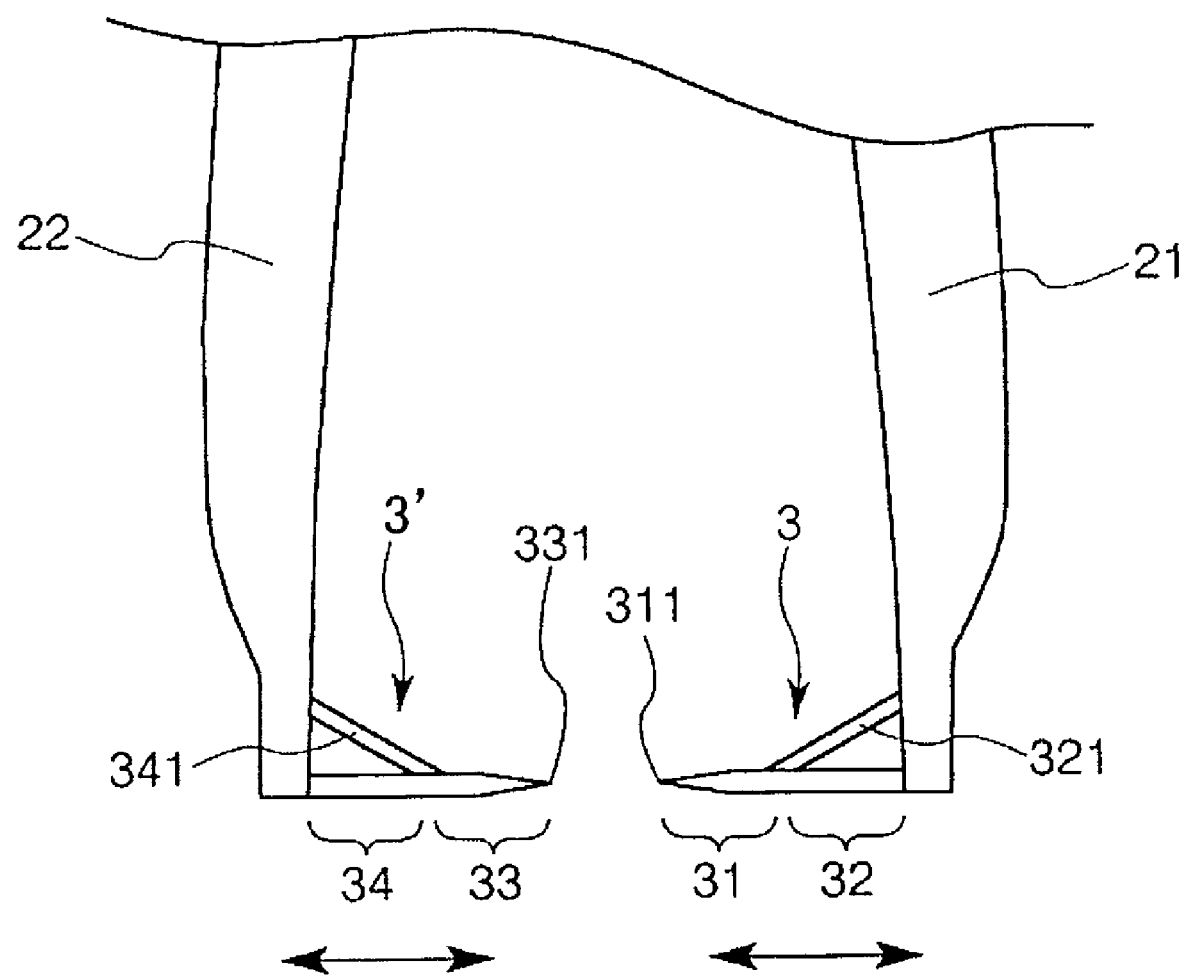
FIG. 35 a side view of the bottom of the apparatus of FIG. 34.

FIG. 34 is a cross-sectional view of a sixth embodiment of the vascular incision apparatus of the invention, and FIG. 35 a side view of the bottom of the apparatus shown in FIG. 34.

The sixth embodiment of the inventive vascular incision apparatus is described below with particular reference to those features which differ from the above-described fifth embodiment of the invention. Descriptions of like features are omitted. In FIGS. 34 and 35, the puncturing and cutting member side of the vascular incision apparatus is referred to as the "bottom end" or "bottom," and the side where the pair of handles are joined to each other is referred to as the top end" or "top."

As illustrated in these diagrams, in the sixth embodiment of the inventive vascular incision apparatus 1, the first needle 31 and the second needle 33 are each provided on proximal end sides thereof with respective cutters 32 and 34 for making an incision in the blood vessel.

A first puncturing and cutting member 3 composed of a first needle 31 having a sharp point on the distal end thereof and a cutter 32 provided on the proximal end side of the first needle 31 is joined to the bottom end of the first handle 21. A second puncturing and cutting member 3' composed of a second needle 33 having a sharp point on the distal end thereof and a cutter 34 provided on the proximal end side of the second needle 33 is joined to the bottom end of the second handle 22. The cutter 34 is substantially triangular in side shape. The blade 341 is formed on the top of the cutter 34. In another arrangement, the cutter 34 may be composed of a section which is an extension of the second needle 33 and a blade 341 formed on the top side of the extension. In this arrangement, the extension and the blade 341 are joined together at the distal ends thereof, and the extension and the blade 341 are separately joined at their respective proximal ends to the bottom end of the second handle 22, giving the cutter 34 a substantially triangular shape.

The advantageous effects provided by this vascular incision apparatus 1 are similar to the effects achievable with the fifth embodiment of the inventive apparatus described above.

Moreover, in this vascular incision apparatus 1, cutters 32 and 34 are provided on the first needle 31 and the second needle 33 respectively, thereby enabling an incision to be made in the blood vessel regardless of whether the apparatus 1 is advanced distally with respect to the first needle 31 (leftward in FIG. 34) or distally with respect to the second needle 33 (rightward in FIG. 34).

Hence, for example, if there should be an obstacle to the vascular incision apparatus 1 in the left or right direction in FIG. 34, an incision can be made in the blood vessel by advancing the apparatus 1 in the other direction.

As in the above-described fifth embodiment, the needles in this sixth embodiment may have the configurations shown in FIGS. 26 to 33. Other variations and modifications of the type discussed above in connection with the fifth embodiment may similarly be applied here.

Next, a seventh embodiment of the vascular incision apparatus of the invention is described.

Figure 36:
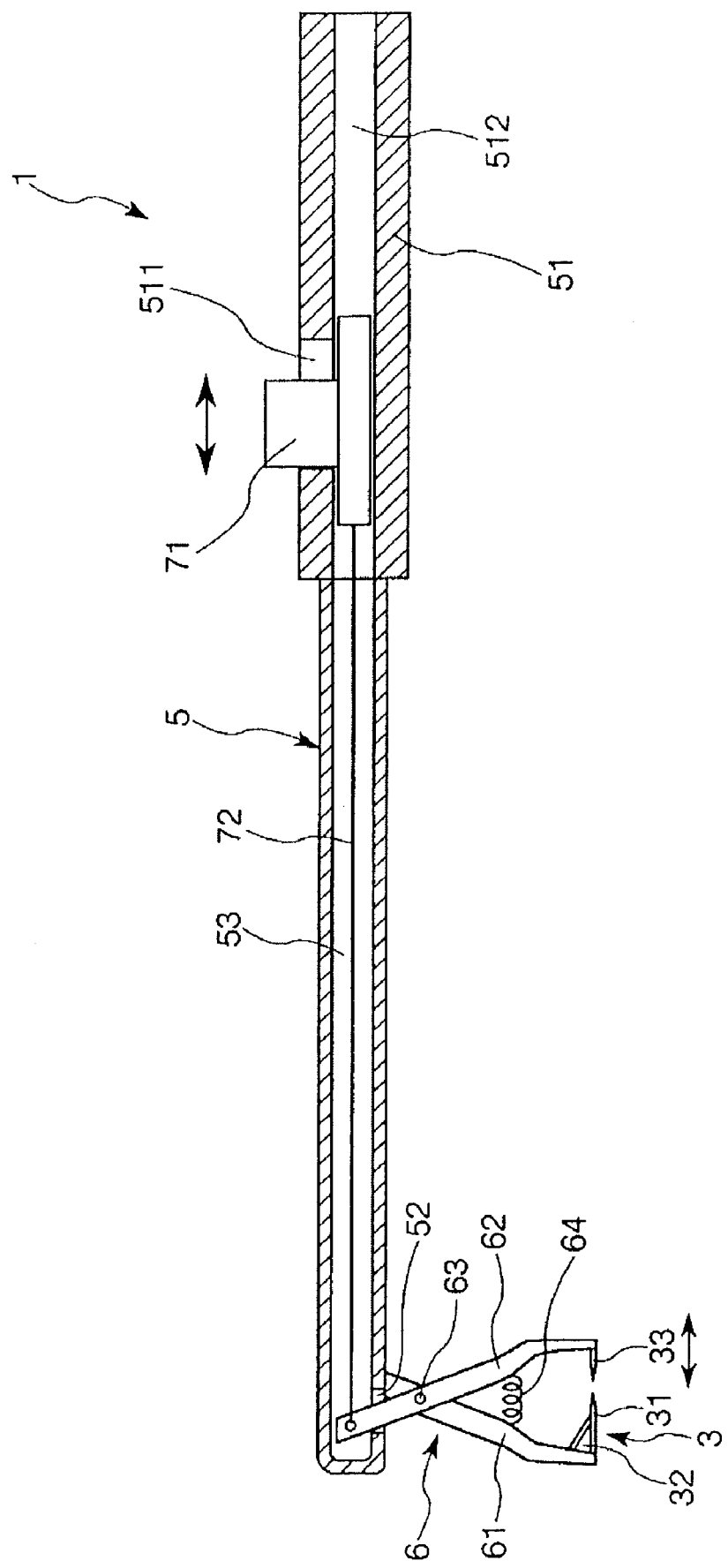
FIGS. 36 and 37 are cross-sectional views of a seventh embodiment of the vascular incision apparatus of the invention.
Figure 37:
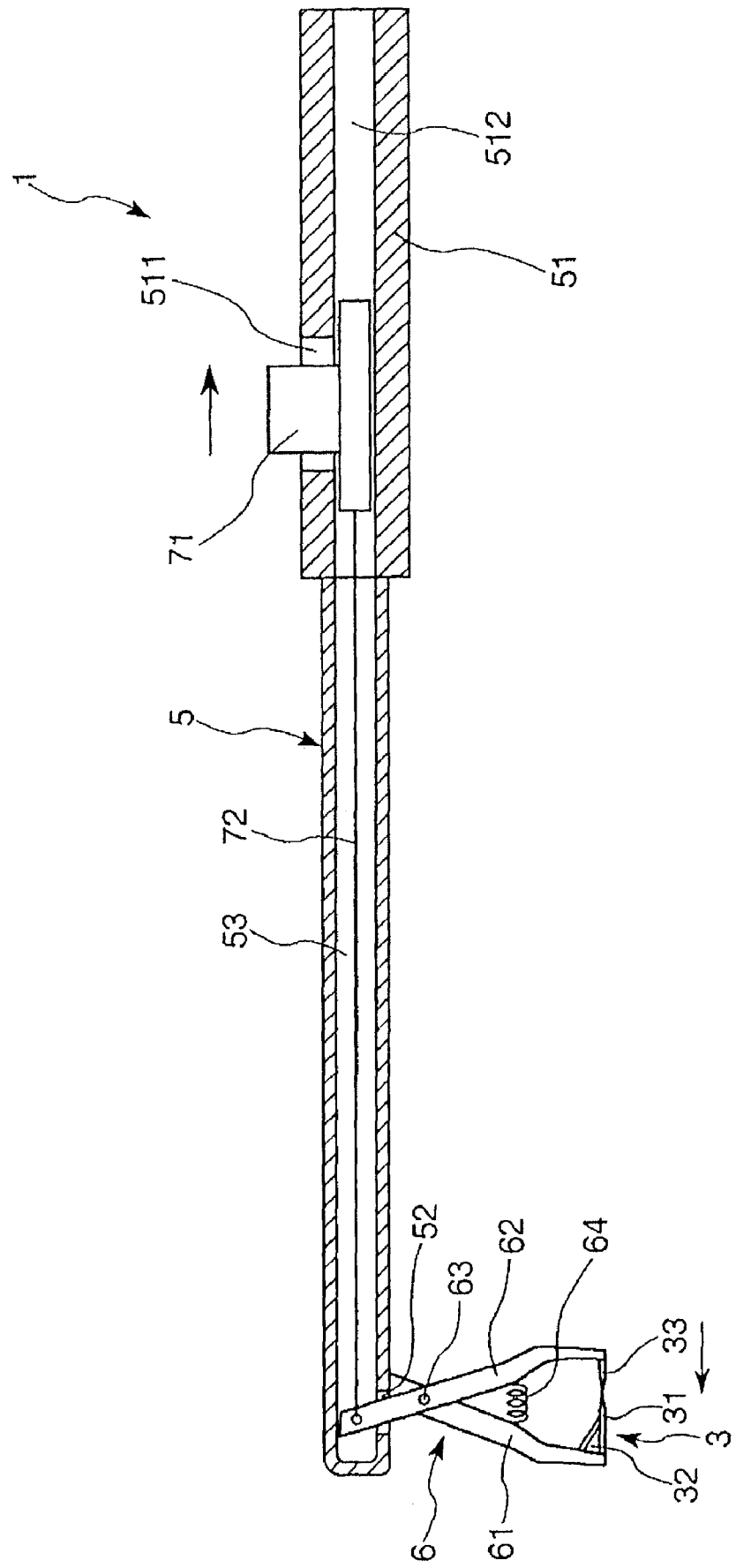

FIGS. 36 and 37 are cross-sectional views of a seventh embodiment of the vascular incision apparatus of the invention.

The seventh embodiment of the inventive vascular incision apparatus is described below with particular reference to those features which differ from the above-described fifth embodiment of the invention. Descriptions of like features are omitted. In FIGS. 36 and 37, the side where a support in the vascular incision apparatus is joined to the puncturing and cutting member is referred to as the "bottom end" or "bottom," the side where supports of the apparatus are joined to the body is referred to as the top end" or "top," the end where the body of the apparatus is joined to the supports is referred to as the "distal end," and the end where the body is joined to a grip is referred to as the "proximal end."

As shown in these diagrams, the seventh embodiment of the vascular incision apparatus 1 has a tubular, elongated body 5.

The body 5 has at a proximal end thereof a grip 51 which the user grasps with the hand and fingers, and has at a distal end thereof a puncturing and cutting means 6.

The puncturing and cutting means 6 has a first support 61 fixedly attached to the body 5, and a second support 62 which is rotatable about a pivot 63 provided on the first support 61. The first and second supports 61, 62 each have a bottom end, with the bottom end of the first support 61 situated on the distal end side of the body 5 relative to the bottom end of the second support 62.

These first and second supports 61, 62 may be made of any suitable material, examples of which include various metals (e.g., stainless steel, titanium, steel, iron, and alloys thereof).

A puncturing and cutting member 3 having a first needle 31 and a cutter 32 is joined to the bottom end of the first support 61, and a second needle 33 is joined to the bottom end of the second support 62.

A coil spring 64 is provided as an urging means in a contracted state between the first and second supports 61 and 62 at a position below the pivot 63. The second support 62 is urged by the elastic force (restoring force) of this coil spring 64 in the counterclockwise rotating direction in FIG. 36; that is, in the direction that separates the bottom end of the first support 61 from the bottom end of the second support 62 (the direction that separates a needle point 311 on the first needle 31 from a needle point 331 on the second needle 33).

The second support 62 has a top end which is inserted into a hollow portion 53 of the body 5 through an opening 52 formed on the bottom side at the distal end of the body 5. The top end of the second support 62 comes up against the distal edge of the opening 52, thereby holding the first needle 31 and the second needle 33 in a state of maximum separation.

An actuating element 71 is provided within a hollow portion 512 of the grip 51 such as to be movable in the lengthwise direction of the grip 51, toward both the distal and proximal ends of the grip 51. This actuating element 71 has a top end which protrudes upward and outward from an opening 511 formed in the top side of the grip 51.

The actuating element 71 is coupled on the distal end side thereof with the top end of the second support 62 by a wire (coupling member) 72 which passes through the hollow portion 512 of the grip 51.

The actuating element 71 and the wire 72 together comprise a control means. Of course, the coupling member is not limited to a wire.

As shown in FIG. 37, when the actuating element 71 is moved proximally (direction of arrow), the top end of the second support 62 is pulled proximally. This induces the second support 62 to rotate clockwise in FIG. 37, causing the second needle 33 to move in a direction that brings the point 311 on the first needle 31 and the point 331 on the second needle 33 closer together.

When the user removes his or her finger from the actuating element 71 or applies less force to the actuating element 71, as shown in FIG. 36, the second support 62 rotates counterclockwise in FIG. 36 under the elastic force of the coil spring 64, causing the bottom ends of the first and second supports 61, 62 to mutually separate and the top end of the second support 62 to come up against the distal edge of the opening 52, thus placing the first needle 31 and the second needle 33 in the maximum separation state.

The advantageous effects provided by this vascular incision apparatus 1 are similar to the effects achievable with the fifth embodiment of the inventive apparatus described above.

Moreover, in this vascular incision apparatus 1, the puncturing and cutting means 6 can be remotely controlled, thus making it possible to create an incision even if there is an obstacle near where the incision is to be made on the blood vessel.

In one alternative arrangement of the apparatus 1 according to this embodiment of the invention, the first support 61 may be rotatable. In another alternative arrangement, the first support 61 and the second support 62 may each be rotatable.

As in the above-described fifth embodiment, the needles in this seventh embodiment may have the configurations shown in FIGS. 26 to 31. Other variations and modifications of the type discussed above in connection with the fifth embodiment may similarly be applied here.

Next, an eighth embodiment of the vascular incision apparatus of the invention is described.

Figure 38:
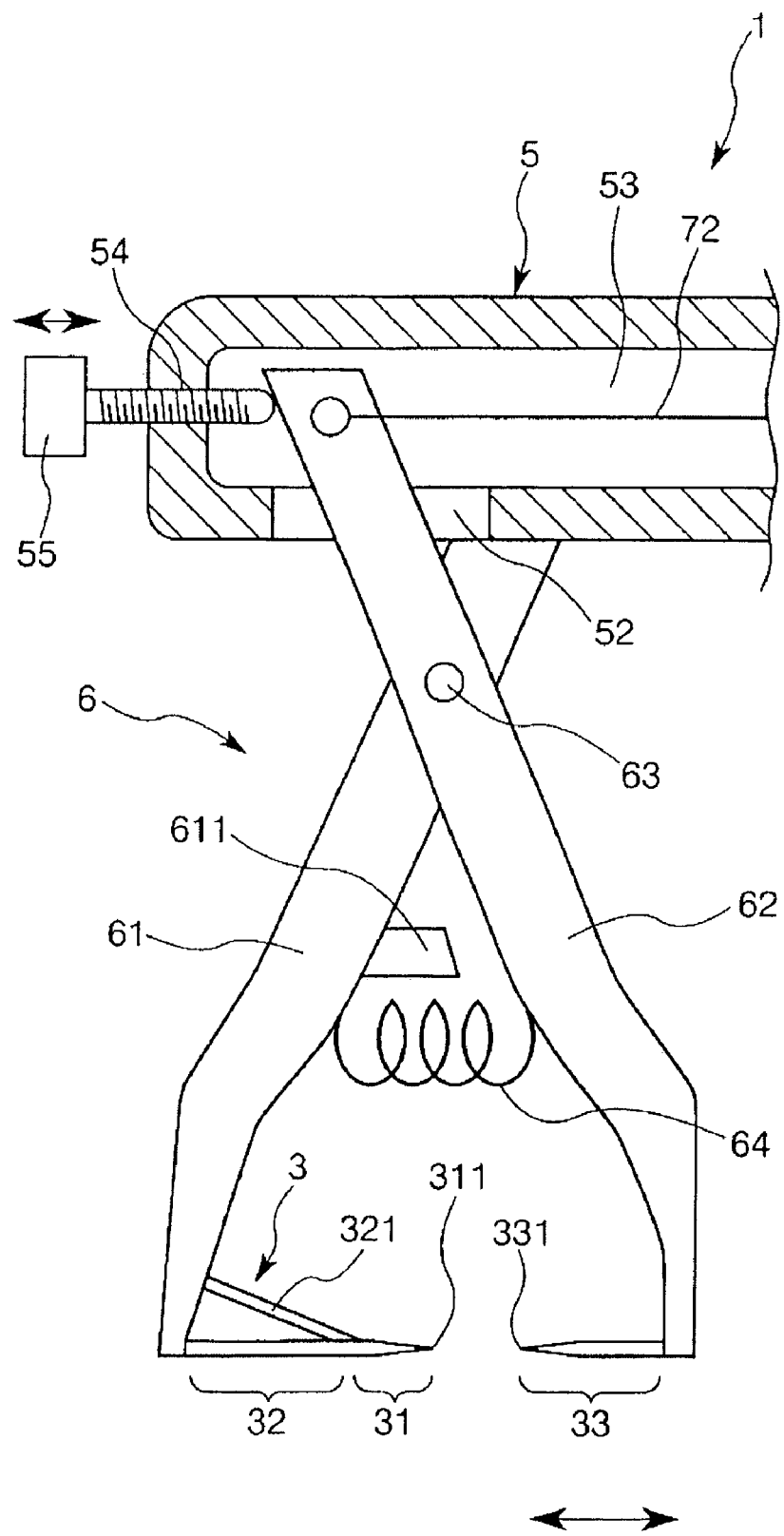
FIG. 38 is a cross-sectional view of the distal end (working end) in an eighth embodiment of the vascular incision apparatus of the invention.

FIG. 38 is a cross-sectional view of the working or distal end in an eighth embodiment of the vascular incision apparatus of the invention.

The eighth embodiment of the inventive vascular incision apparatus 1 is described below with particular reference to those features which differ from the above-described seventh embodiment of the invention. Descriptions of like features are omitted. In FIG. 38, the side where a support in the vascular incision apparatus is joined to the puncturing and cutting member is referred to as the "bottom end" or "bottom," the side where the supports are joined to the body of the apparatus is referred to as the top end" or "top." The left side with respect to the thus-defined "bottom" and "top" of the apparatus is referred to herein as the "distal end," and the right side as the "proximal end."

As shown in FIG. 38, the eighth embodiment of the vascular incision apparatus 1 has, on the second support 62 side of the first support 61, a stop 611 which functions as a closest approach state controlling means and is situated below a pivot 63.

A screw hole 54 is formed at the distal end of the body 5, and a screw 55 is threadedly engaged with the screw hole 54.

When the top end of the second support 62 comes up against this screw 55, the first needle 31 and the second needle 33 are held in a state of maximum separation therebetween.

Turning the screw 55 causes it to move in the left-right direction in FIG. 38, which alters the maximum separation state, thus changing the maximum distance between the point 311 on the first needle 31 and the point 331 on the second needle 33.

Moving the screw 55 rightward in FIG. 38, that is, toward the proximal side of the body 5, decreases the maximum distance, resulting in a shorter incision length. Conversely, moving the screw 55 leftward in FIG. 38, that is, toward the distal side of the body 5, increases the maximum distance, resulting in a longer incision length.

Accordingly, the screw 55 functions as a maximum separation state controlling means that controls the maximum separation state between the first needle 31 and the second needle 33, and also as an incision length adjusting mechanism which adjusts the maximum distance between the point 311 on the first needle 31 and the point 331 on the second needle 33.

When an actuating element (not shown) is moved proximally (rightward in FIG. 38), the top end of the second support 62 is pulled proximally (rightward in FIG. 38) by a wire 72. This causes the second support 62 to rotate clockwise in FIG. 38, as a result of which the second needle 33 moves in a direction that brings the point 311 on the first needle 31 and the point 331 on the second needle 33 closer together. When the second support 62 reaches the stop 611, the first needle 31 and the second needle 33 are in their closest approach state.

The advantageous effects provided by this vascular incision apparatus 1 are similar to the effects achievable with the seventh embodiment of the inventive apparatus described above.

In this vascular incision apparatus 1, the stop 611 helps prevent damage to the point 311 on the first needle 31 and the point 331 on the second needle 33. Moreover, the incision length in the blood vessel can be easily and reliably adjusted by turning the screw 55.

As in the above-described fifth embodiment, the needles in this eighth embodiment may have the configurations shown in FIGS. 26 to 33. Other variations and modifications of the type discussed above in connection with the fifth embodiment may similarly be applied here.

Next, a ninth embodiment of the vascular incision apparatus of the invention is described.

Figure 39:
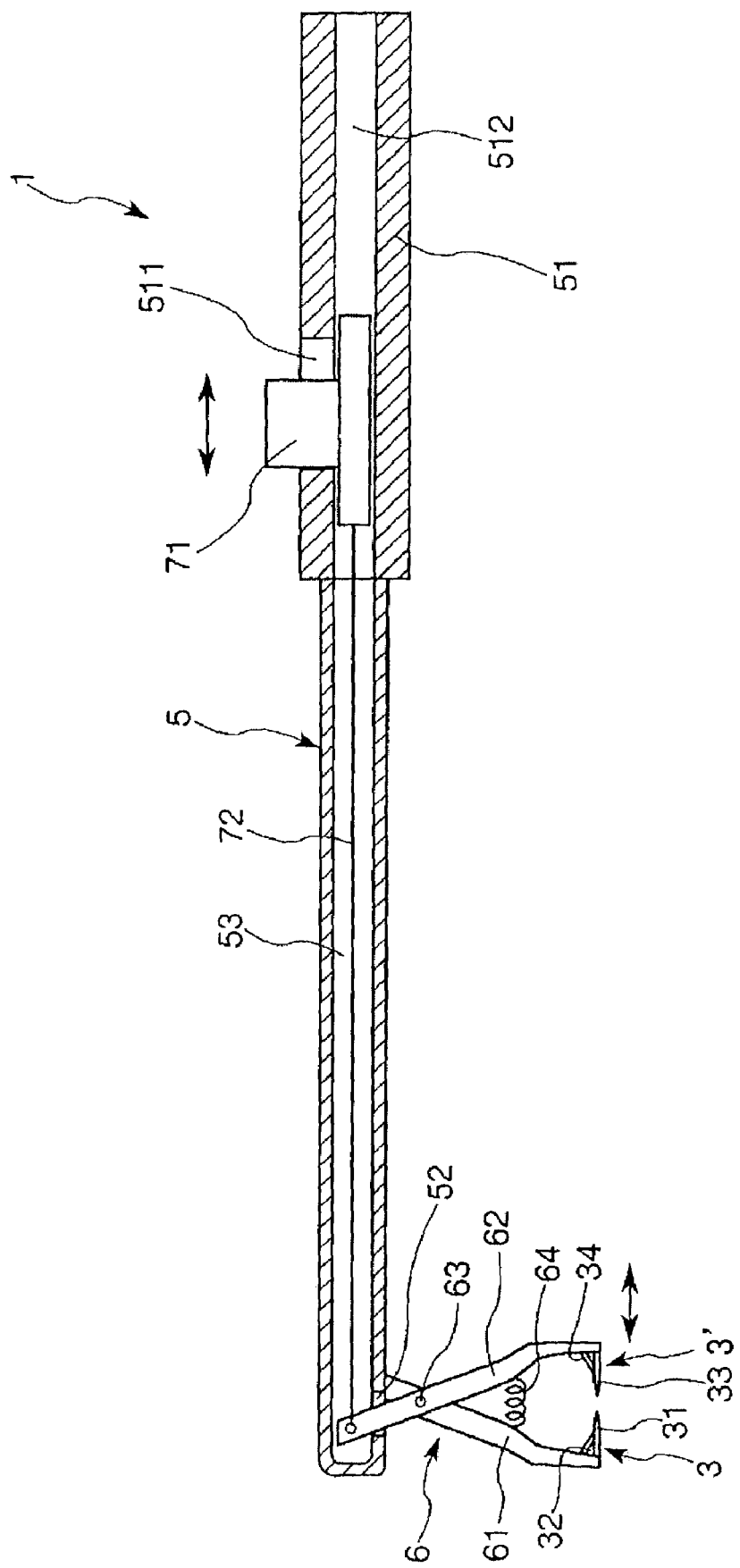
FIG. 39 is a cross-sectional view of a ninth embodiment of the vascular incision apparatus of the invention.

FIG. 39 is a cross-sectional view of a ninth embodiment of the vascular incision apparatus of the invention.

The ninth embodiment of the inventive vascular incision apparatus 1 is described below with particular reference to those features which differ from the above-described seventh embodiment of the invention. Descriptions of like features are omitted. In FIG. 39, the side where supports in the vascular incision apparatus are joined to puncturing and cutting members is referred to as the "bottom end" or "bottom," and the side where the supports are joined to the body of the apparatus is referred to as the top end" or "top."

As shown in FIG. 39, the ninth embodiment of the vascular incision apparatus 1 is provided with a cutter 32 on the proximal end side of a first needle 31 and a cutter 34 on the proximal end side of a second needle 33, which cutters 32, 34 are for making an incision in the blood vessel.

That is, a first support 61 has joined, at the lower end thereof, a first puncturing and cutting member 3 composed of a first needle 31 having a sharp point at the distal end thereof and a cutter 32 provided on the proximal end side of the first needle 31. A second support 62 has joined, at the lower end thereof, a second puncturing and cutting member 3' composed of a second needle 33 having a sharp point at the distal end thereof and a cutter 34 provided on the proximal end side of the second needle 33.

The advantageous effects provided by this vascular incision apparatus 1 are similar to the effects achievable with the seventh embodiment of the inventive apparatus described above.

Moreover, in this vascular incision apparatus 1, the presence of a cutter 32 on the first needle 31 and another cutter 34 on the second needle 33 enables an incision to be made in the blood vessel regardless of whether the apparatus 1 is advanced distally with respect to the first needle 31 (rightward in FIG. 39) or distally with respect to the second needle 33 (leftward in FIG. 39).

As in the above-described fifth embodiment, the needles in this ninth embodiment may have the configurations shown in FIGS. 26 to 31. Moreover, as in the eighth embodiment described above, it is advantageous to provide also a stop 611 and a screw 55. Other variations and modifications of the type discussed above in connection with the fifth embodiment may similarly be applied here.

Next, a tenth embodiment of the vascular incision apparatus of the invention is described.

Figure 40:
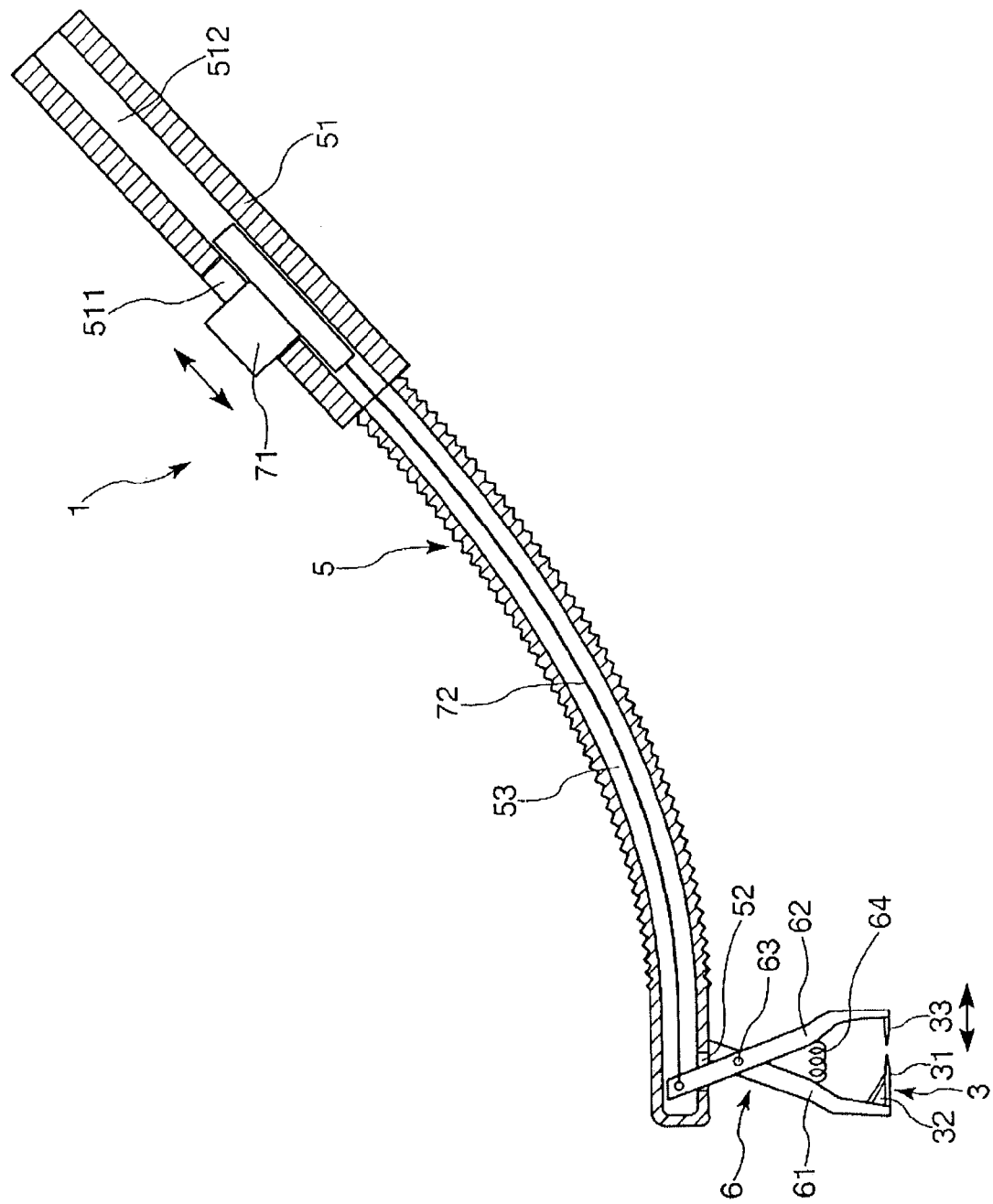
FIG. 40 is a cross-sectional view of a tenth embodiment of the vascular incision apparatus of the invention.

FIG. 40 is a cross-sectional view of a tenth embodiment of the vascular incision apparatus of the invention.

The tenth embodiment of the inventive vascular incision apparatus is described below with particular reference to those features which differ from the above-described seventh embodiment of the invention. Descriptions of like features are omitted. In FIG. 40, the side where a support in the vascular incision apparatus is joined to a puncturing and cutting member is referred to as the "bottom end" or "bottom," the side where supports are joined to the body of the apparatus is referred to as the top end" or "top," the end where the body of the apparatus is joined to the supports is referred to as the "distal end," and the end where the body is joined to a grip is referred to as the "proximal end."

As shown in FIG. 40, in the tenth embodiment of the vascular incision apparatus 1, the body 5 has a grip 51 and a distal end. The portion of the body 5 between the grip 51 and the distal end is laterally deformable (i.e., capable of being curved or bent) with respect to the lengthwise direction of the body 5, and is constructed so as to be capable of retaining the deformed shape. In the illustrated arrangement, the portion of the body 5 between the grip 51 and the distal end has a flexible corrugated construction.

The advantageous effects provided by this vascular incision apparatus 1 are similar to the effects achievable with the seventh embodiment of the inventive apparatus described above.

Moreover, compared with the seventh embodiment, the vascular incision apparatus 1 according to the present embodiment provides the advantage that when a difficult-to-avoid obstacle is located near the target incision site in the blood vessel, the obstacle can be avoided by deforming the body 5 of the apparatus 1, making it possible to create an incision at the desired site.

As in the above-described fifth embodiment, the needles in the present embodiment may have the configurations shown in FIGS. 26 to 31. Moreover, as in the eighth embodiment described above, it is advantageous to provide a stop 611 and a screw 55. Other variations and modifications of the type discussed above in connection with the fifth embodiment may similarly be applied here.

Next, an eleventh embodiment of the vascular incision apparatus of the invention is described.

Figure 41:
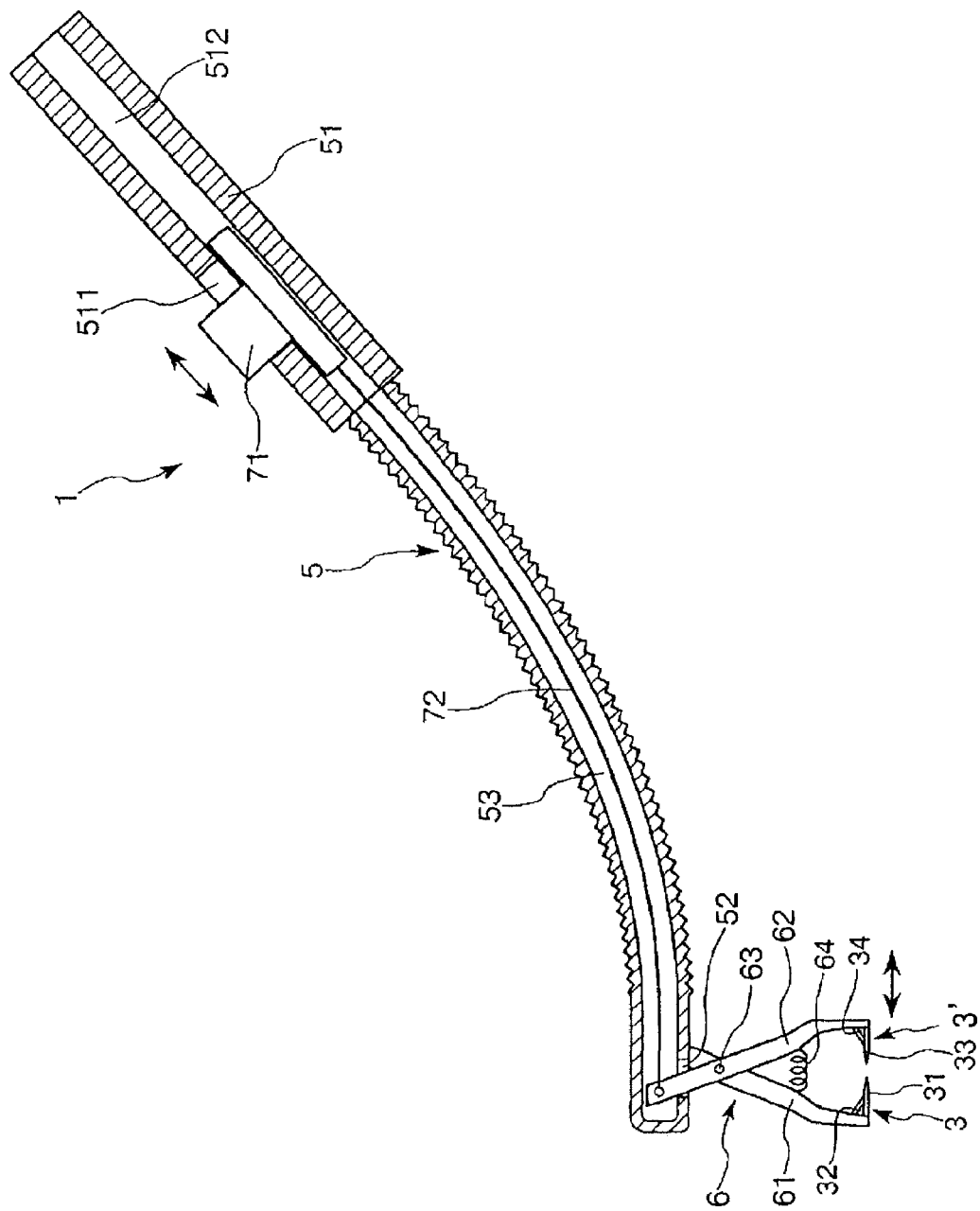
FIG. 41 is a cross-sectional view of an eleventh embodiment of the vascular incision apparatus of the invention.

FIG. 41 is a cross-sectional view of an eleventh embodiment of the vascular incision apparatus of the invention.

The eleventh embodiment of the inventive vascular incision apparatus is described below with particular reference to those features which differ from the above-described tenth embodiment of the invention. Descriptions of like features are omitted. In FIG. 41, the side where supports in the vascular incision apparatus are joined to puncturing and cutting members is referred to as the "bottom end" or "bottom," and the side where the supports are joined to the body of the apparatus is referred to as the top end" or "top."

As shown in FIG. 41, the eleventh embodiment of the vascular incision apparatus 1 is provided with a cutter 32 on the proximal end side of a first needle 31 and a cutter 34 on the proximal end side of a second needle 33, which cutters 32, 34 are for making an incision in the blood vessel.

That is, a first support 61 has joined, at the lower end thereof, a first puncturing and cutting member 3 composed of a first needle 31 having a sharp point at the distal end thereof and a cutter 32 provided on the proximal end side of the first needle 31. A second support 62 has joined, at the lower end thereof, a second puncturing and cutting member 3' composed of a second needle 33 having a sharp point at the distal end thereof and a cutter 34 provided on the proximal end side of the second needle 33.

The advantageous effects provided by this vascular incision apparatus 1 are similar to the effects achievable with the tenth embodiment of the inventive apparatus described above.

Moreover, in this vascular incision apparatus 1, the presence of a cutter 32 on the first needle 31 and another cutter 34 on the second needle 33 enables an incision to be made in the blood vessel regardless of whether the apparatus 1 is advanced distally with respect to the first needle 31 (rightward in FIG. 39) or distally with respect to the second needle 33 (leftward in FIG. 39).

As in the above-described fifth embodiment, the needles in this eleventh embodiment may have the configurations shown in FIGS. 26 to 31. Moreover, as in the eighth embodiment described above, it is advantageous to provide also a stop 611 and a screw 55. Other variations and modifications of the type discussed above in connection with the fifth embodiment may similarly be applied here.

Next, a twelfth embodiment of the vascular incision apparatus of the invention is described.

Figure 42:
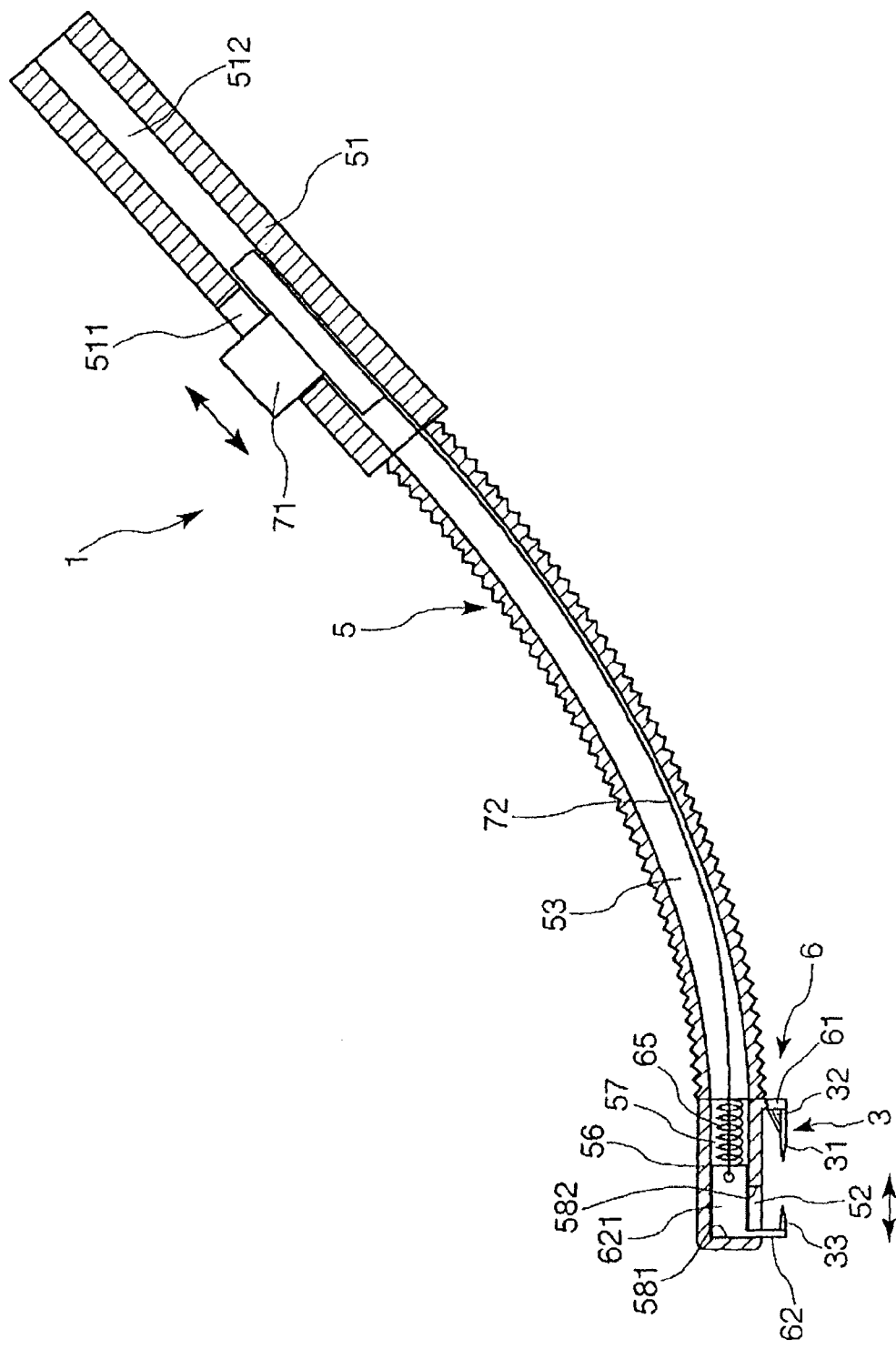
FIG. 42 is a cross-sectional view of a twelfth embodiment of the vascular incision apparatus of the invention.
Figure 43:
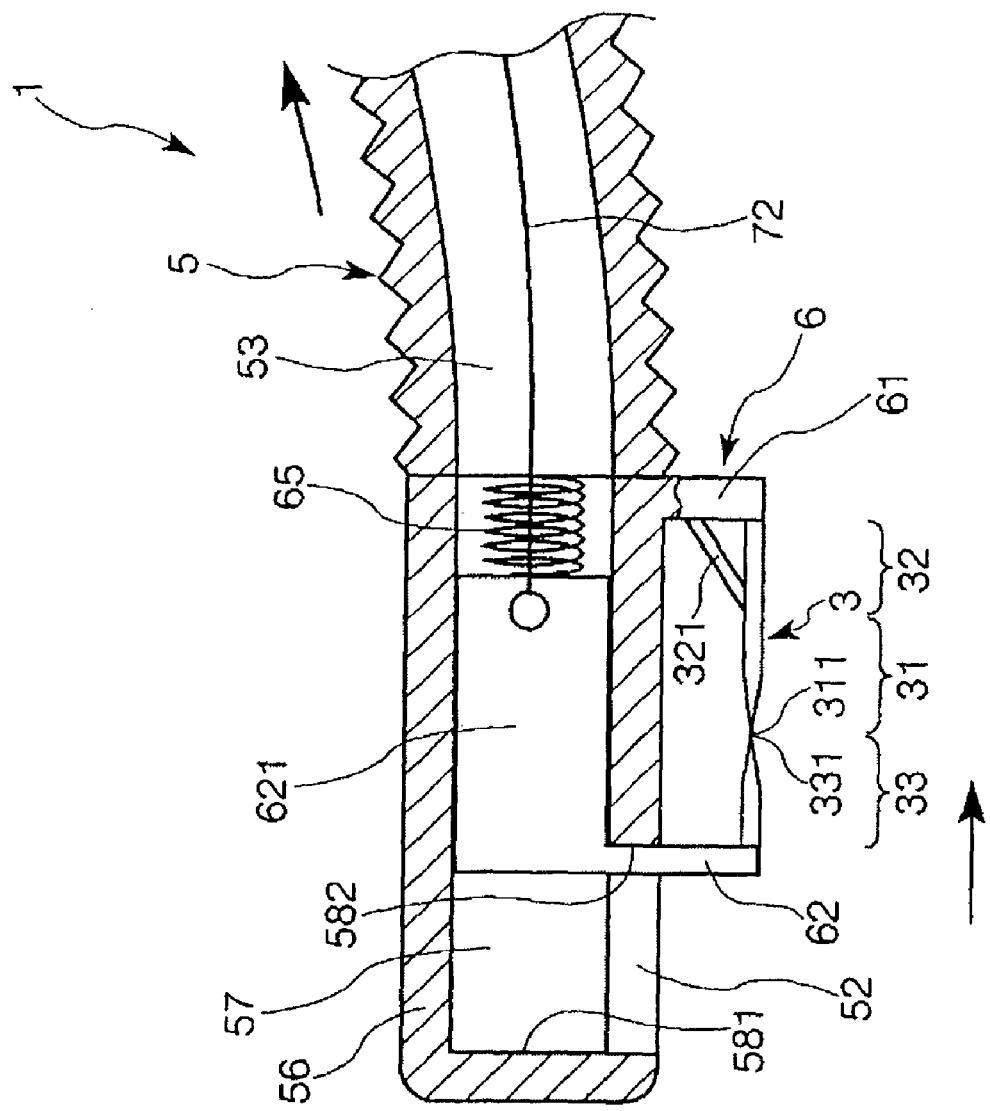
FIG. 43 is a cross-sectional view of the distal end (working end) of the apparatus of FIG. 42.

FIG. 42 is a cross-sectional view of a twelfth embodiment of the vascular incision apparatus of the invention, and FIG. 43 is a cross-sectional view of the distal end (working end) of the apparatus of FIG. 42.

The twelfth embodiment of the inventive vascular incision apparatus 1 is described below with particular reference to those features which differ from the above-described tenth embodiment of the invention. Descriptions of like features are omitted. In FIGS. 42 and 43, the side where a support in the vascular incision apparatus is joined to a puncturing and cutting member is referred to as the "bottom end" or "bottom," and the side where supports are joined to the body of the apparatus is referred to as the top end" or "top." The left end with respect to the thus-defined "bottom" and "top" of the apparatus is referred to herein as the "distal end," and the right end as the "proximal end."

As shown in these diagrams, in the twelfth embodiment of the vascular incision apparatus 1, an incision and cutting means 6 has a support 61 fixedly attached to a distal, or working, end 56 of the body 5, and a support 62 provided on the working end of the body 5 such as to be movable in the lengthwise direction of the body 5 (in both the distal and proximal directions relative to the body 5). The first support 61 projects downward from the working end 56 of the body 5, and is situated at a position on the body 5 which is proximal to the second support 62.

The second support 62 has at the top end thereof a slider 621 which is disposed within a hollow area 57 at the working end 56 of the body 5 such as to be movable in the lengthwise direction of the body (in both the distal and proximal directions relative to the body 5).

The proximal end of the slider 621 is coupled to the distal end of an actuating element 71 by means of a wire (coupling member) 72 which traverses hollow areas 57 and 53 in the body 5 and a hollow area 512 in a grip 51.

The working end 56 of the body 5 has an opening 52 formed on a lower side thereof. A bottom end side of second support 62 projects downward and outward through opening 52.

A puncturing and cutting member 3 is joined to the bottom end of first support 61, and a second needle 33 is joined to the bottom end of second support 62.

A coil spring (urging means) 65 is provided in a contracted state within the hollow area 57 at the working end 56 of the body 5, between the proximal side of the working end 56 and the slider 621. The slider 621 and the second support 62 are urged toward the distal side of the working end 56 by the elastic force (restoring force) of the coil spring 65. That is, the coil spring 65 urges apart the first support 61 and the second support 62 (in a direction that separates the point 311 on the first needle 31 and the point 331 on the second needle 33).

When the top end of the second support 62 and the slider 621 reach an inside wall (maximum separation state controlling means) 581 on the distal side of the working end 56, the first needle 31 and the second needle 33 are held in a state of maximum separation.

As shown in FIG. 43, moving the actuating element 71 in the proximal direction causes the wire 72 to pull slider 621 proximally, resulting in movement by the slider 621 and the second support 62 toward the proximal end. That is, the second needle 33 moves in a direction that brings the point 311 on the first needle 31 and the point 331 on the second needle 33 closer together. When the top end of the second support 62 reaches the proximal edge (closest approach state controlling means) 582 of the opening 52, the first needle 31 and the second needle 33 are in their state of closest approach.

When the user removes his or her finger from the actuating element 71 or applies less force to the actuating element 71, as shown in FIG. 42, the slider 621 and the second support 62 move toward the distal side of the working end 56 by the elastic force of the coil spring 65. When the top end of the second support 62 and the slider 621 reach an inside wall (maximum separation state controlling means) 581 on the distal side of the working end 56, the first needle 31 and the second needle 33 are in a state of maximum separation.

The advantageous effects provided by this vascular incision apparatus 1 are similar to the effects achievable with the tenth embodiment of the inventive apparatus described above.

Moreover, in this vascular incision apparatus 1, movement of the slider 621 and the second support 62 in the lengthwise direction of the working end 56 causes the first needle 31 and the second needle 33 to mutually separate or approach each other, enabling more precise and reliable control of the incision length.

In addition, by using the proximal edge 582 of opening 52 to control the maximum separation state, damage to point 311 on first needle 31 and point 331 on second needle 33 can be reliably prevented.

In alternative versions of this embodiment of the invention, it is possible to make first support 61 movable rather than second support, or to make both first and second supports 61 and 62 movable.

As in the above-described fifth embodiment, the needles in this twelfth embodiment may have the configurations shown in FIGS. 26 to 31. Moreover, as in the eighth embodiment described above, it is advantageous to provide a maximum separation state controlling means or an incision length adjusting mechanism such as a screw 55. Other variations and modifications of the type discussed above in connection with the fifth embodiment may similarly be applied here.

Next, a thirteenth embodiment of the vascular incision apparatus of the invention is described.

Figure 44:
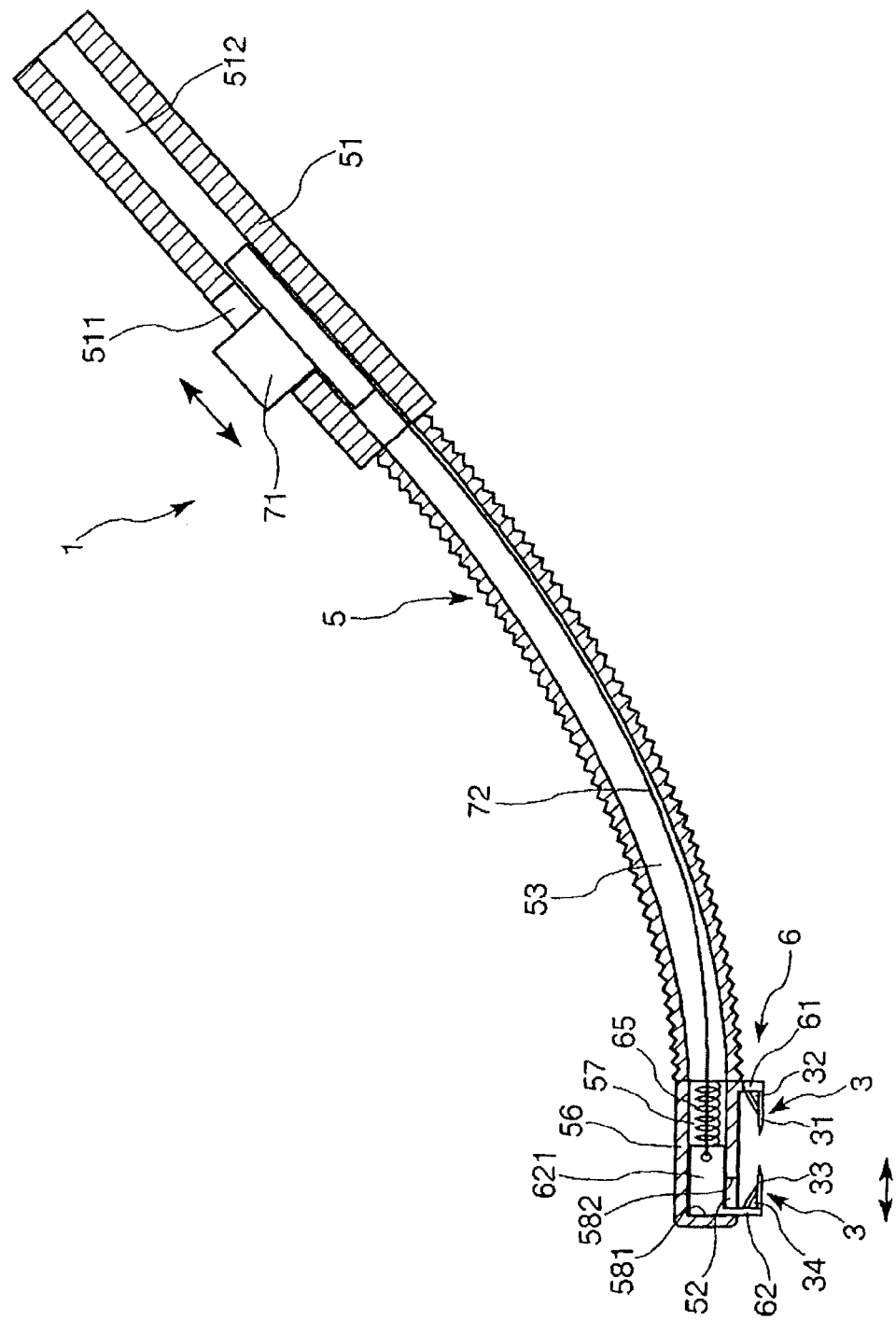
FIG. 44 is a cross-sectional view of a thirteenth embodiment of the vascular incision apparatus of the invention.

FIG. 44 is a cross-sectional view of a thirteenth embodiment of the vascular incision apparatus of the invention.

The thirteenth embodiment of the inventive vascular incision apparatus is described below with particular reference to those features which differ from the above-described twelfth embodiment of the invention. Descriptions of like features are omitted. In FIG. 44, the side where supports in the vascular incision apparatus are joined to puncturing and cutting members is referred to as the "bottom end" or "bottom," and the side where the supports are joined to the body of the apparatus is referred to as the top end" or "top."

As shown in FIG. 44, the thirteenth embodiment of the vascular incision apparatus 1 is provided with a cutter 32 on the proximal end of a first needle 31 and a cutter 34 on the proximal end of a second needle 33, which cutters 32, 34 are for making an incision in the blood vessel.

That is, a first support 61 has joined, at the lower end thereof, a first puncturing and cutting member 3 composed of a first needle 31 having a sharp point at the distal end thereof and a cutter 32 provided at the proximal end side of the first needle 31. A second support 62 has joined, at the lower end thereof, a second puncturing and cutting member 3' composed of a second needle 33 having a sharp point at the distal end thereof and a cutter 34 provided at the proximal end side of the second needle 33.

The advantageous effects provided by this vascular incision apparatus 1 are similar to the effects achievable with the twelfth embodiment of the inventive apparatus described above.

Moreover, in this vascular incision apparatus 1, the presence of a cutter 32 on the first needle 31 and another cutter 34 on the second needle 33 enables an incision to be made in the blood vessel regardless of whether the apparatus 1 is advanced distally with respect to the first needle 31 (rightward in FIG. 44) or distally with respect to the second needle 33 (leftward in FIG. 44).

As in the above-described fifth embodiment, the needles in this thirteenth embodiment may have the configurations shown in FIGS. 26 to 31. Moreover, as in the eighth embodiment described above, it is advantageous to provide an incision length adjusting mechanism, or a maximum separation state controlling means having an incision length adjusting mechanism, such as a screw 55. Other variations and modifications of the type discussed above in connection with the fifth embodiment may similarly be applied here.

The illustrated embodiments of the vascular incision apparatus of the invention have been described above, although many modifications and variations may be made thereto in light of the above teachings. It is therefore to be understood that the invention may be practiced otherwise than as specifically described without departing from the scope of the appended claims. For example, various parts of the apparatus having the specific configurations shown and described herein may be substituted with parts of other configurations with similar functions.

The invention also encompasses vascular incision apparatuses which combine any two or more of the configurations described above in connection with the foregoing embodiments.

As noted above, an incision of the target (desired) length can be easily, rapidly and reliably created in a blood vessel with the inventive vascular incision apparatus having an incision length controlling means because the incision length controlling means controls the length of the incision made in the blood vessel by the puncturing and cutting member.

If the vascular incision apparatus also has an incision length adjusting mechanism for adjusting the blood vessel incision length controlled by the incision length controlling means, the incision length in the blood vessel can be easily, rapidly and reliably set to the desired length.

Moreover, if the vascular incision apparatus has a puncturing and cutting member that is movable with respect to the body of the apparatus and a control means that actuates movement by the puncturing and cutting member, the wall of the blood vessel can be cut by moving the puncturing and cutting member without having to move the body of the apparatus, thus enabling an incision to be more easily and rapidly created in the blood vessel.

When use is made of a vascular incision apparatus according to the invention that has a first and a second needle, the incision length in the blood vessel is controlled by the point on the first needle and the point on the second needle, enabling the blood vessel to be easily, rapidly and reliably incised to the desired length.

What is claimed is:

1. A vascular incision apparatus comprising:
a body;
a puncturing and cutting member having a needle with a sharp point for penetrating a blood vessel and a cutter for making an incision in the blood vessel, which cutter is disposed proximal to the needle;
incision length controlling means for controlling the length of the incision made by the puncturing and cutting member; and
the incision length controlling means has a stopper arm with a stop thereon that comes into resting contact with the puncturing and cutting member at a boundary between the needle and the cutter or at the needle; wherein said contact by the stop with the puncturing and cutting member controls the length of penetration by the needle into the blood vessel and said stopper arm is provided such as to enable repositioning thereof relative to the puncturing and cutting member between a first position which prevents the cutter from cutting the blood vessel and a second position which allows the cutter to cut the blood vessel.

2. The apparatus of claim 1, wherein the stop separates away from the puncturing and cutting member when the stopper arm assumes the second position.

3. The apparatus of claim 1 which has restoring means for returning the stopper arm to the first position.

4. The apparatus of claim 1, wherein the puncturing and cutting member is disposed at one end of the body and the stopper arm is linearly movable with respect to the body.

5. The apparatus of claim 1, wherein the puncturing and cutting member is disposed at one end of the body and the stopper arm is rotatable with respect to the body.

6. The apparatus of claim 1, in which the puncturing and cutting member is movable with respect to the body, and which has a control member for effecting movement by the puncturing and cutting member.

7. The apparatus of claim 6, wherein repositioning of the stopper arm is coupled to movement by the puncturing and cutting member.

8. The apparatus of claim 1 which has an incision length adjusting mechanism for adjusting the incision length controlled by the incision length controlling means.

9. The apparatus of claim 8, wherein the incision length adjusting mechanism has a holder for holding the stopper arm such as to allow movement thereof in the lengthwise direction of the needle, and a control member for effecting movement by the stopper arm in the lengthwise direction of the needle.

10. The apparatus of claim 1, wherein the needle is curved on at least a distal end thereof.

11. The apparatus of claim 1, wherein the puncturing and cutting member is freely detachable from the body.

12. A vascular incision apparatus comprising:
a body;

a puncturing and cutting member connected to the body, the puncturing and cutting member comprising a needle with a sharp point for penetrating a blood vessel and a cutter for making an incision in the blood vessel, the cutter being disposed proximal to the needle;

incision length controlling means for controlling the length of the incision made by the puncturing and cutting member;

the incision length controlling means comprising a stopper arm movably mounted on the body and a stop on the stopper arm that is positionable in contact with the puncturing and cutting member at a boundary between the needle and the cutter or at the needle to define the length of penetration by the needle into the blood vessel; and a control member connected to the stopper arm and operable to move the stopper arm relative to the puncturing and cutting member between a first position which prevents the cutter from cutting the blood vessel and a second position which allows the cutter to cut the blood vessel.

13. The apparatus of claim 12, wherein the stopper arm is movably mounted on the body by way of a sleeve slidably mounted on a support of the body.

14. The apparatus of claim 12, further comprising restoring means for returning the stopper arm to the first position.

15. The apparatus of claim 12, wherein the stopper arm is rotatably mounted on the body.

16. The apparatus of claim 12, wherein the needle includes a distal end portion that is curved along a longitudinal extent of the needle.

17. The apparatus of claim 12, wherein the puncturing and cutting member is freely detachable from the body.

18. The apparatus of claim 12, in which the puncturing and cutting member is movable with respect to the body.

19. The apparatus of claim 18, wherein movement of the stopper arm is coupled to movement by the puncturing and cutting member.

20. The apparatus of claim 12, further comprising an incision length adjusting mechanism for adjusting the incision length controlled by the incision length controlling means.

21. The apparatus of claim 20, wherein the incision length adjusting mechanism has a holder for holding the stopper arm to allow movement of the stopper arm in a lengthwise direction of the needle.

22. A vascular incision apparatus comprising:
a body;
a puncturing and cutting member connected to the body and comprising a needle with a sharp point for penetrating a blood vessel and a cutter for making an incision in the blood vessel, the cutter being disposed proximal to the needle, the cutter and needle being fixed in position relative to each other at all times;

incision length controlling means for controlling the length of the incision made by the puncturing and cutting member;

the incision length controlling means comprising a stopper arm and a stop on the stopper arm that is positionable in contact with the puncturing and cutting member at a boundary between the needle and the cutter or at the needle to define the length of penetration by the needle into the blood vessel; and the stopper arm being movable relative to the puncturing and cutting member between a first position which prevents the cutter from cutting the blood vessel and a second position which allows the cutter to cut the blood vessel.

23. The apparatus of claim 22, wherein the stopper arm is movably mounted on the body by way of a sleeve slidably mounted on a support of the body.

24. The apparatus of claim 22, further comprising restoring means for returning the stopper arm to the first position.

25. The apparatus of claim 22, wherein the stopper arm is rotatably mounted on the body.

26. The apparatus of claim 22, wherein the needle includes a distal end portion that is curved along a longitudinal extent of the needle.

27. The apparatus of claim 22, wherein the puncturing and cutting member is freely detachable from the body.

28. The apparatus of claim 22, in which the puncturing and cutting member is movable with respect to the body.

29. The apparatus of claim 28, wherein movement of the stopper arm is coupled to movement by the puncturing and cutting member.

30. The apparatus of claim 22, further comprising an incision length adjusting mechanism for adjusting the incision length controlled by the incision length controlling means.

31. The apparatus of claim 30, wherein the incision length adjusting mechanism has a holder for holding the stopper arm to allow movement of the stopper arm in a lengthwise direction of the needle.

* * * * *